US012760077B2

(12) United States Patent
Kungl

(10) Patent No.: US 12,760,077 B2
(45) Date of Patent: Oct. 13, 2026

(54) T-CELL MOBILIZING CXCL10 MUTANT WITH INCREASED GLYCOSAMINOGLYCAN BINDING AFFINITY

(71) Applicant: ANTAGONIS BIOTHERAPEUTICS GMBH, Graz (AT)

(72) Inventor: Andreas Kungl, Graz (AT)

(73) Assignee: ANTAGONIS BIOTHERAPEUTICS GMBH, Graz (AT)

( * ) Notice: Subject to any disclaimer, the term of this patent is extended or adjusted under 35 U.S.C. 154(b) by 193 days.

(21) Appl. No.: 17/631,868

(22) PCT Filed: Aug. 28, 2020

(86) PCT No.: PCT/EP2020/074068
§ 371 (c)(1),
(2) Date: Jan. 31, 2022

(87) PCT Pub. No.: WO2021/038033
PCT Pub. Date: Mar. 4, 2021

(65) Prior Publication Data

US 2022/0281934 A1 Sep. 8, 2022

(30) Foreign Application Priority Data

Aug. 29, 2019 (EP) .................................... 19194257

(51) Int. Cl.
*A61P 35/00* (2006.01)
*A61P 29/02* (2006.01)
*A61P 37/02* (2006.01)
*C07K 14/52* (2006.01)

(52) U.S. Cl.
CPC ............ *C07K 14/521* (2013.01); *A61P 29/02* (2018.01); *A61P 37/02* (2018.01); *C07K 2319/30* (2013.01); *C07K 2319/31* (2013.01)

(58) Field of Classification Search
None
See application file for complete search history.

(56) References Cited

U.S. PATENT DOCUMENTS

2006/0204498 A1* 9/2006 Proudfoot ............... A61P 29/00 536/23.53
2020/0207846 A1* 7/2020 Igawa ....................... A61P 1/16

FOREIGN PATENT DOCUMENTS

WO 2005054285 A1 6/2005

OTHER PUBLICATIONS

Jacobs et al. (2014) Anticancer Research 34: 2689-2700.*
Madkhali et al. (2025) Cancer Biology & Therapy 26(1), 2538962: 1-20.*
Written Opinion of the International Searching Authority for corresponding International Patent Application No. PCT/EP2020/074068 dated Nov. 30, 2020.
International Search Report for corresponding International Patent Application No. PCT/EP2020/074068 dated Nov. 30, 2020.
Adage, T et al., “Structure-based design of decoy chemokines as a way to explore the pharmacological potential of glycosaminoglycans”, Br J Pharmacol., 2012, vol. 167, pp. 1195-1205.
Bernfield, M et al., “Functions of Cell Surface Heparan Sulfate Proteoglycans”, Annual review of biochemistry, 1999, vol. 68, pp. 729-777.
Booth, V et al, “The CXCR3 Binding Chemokine IP-10/CXCL10: Structure and Receptor Interactions”, Biochemistry, 2002, vol. 41, pp. 10418-10425.
Campanella, G S et al., “Oligomerization of CXCL10 Is Necessary for Endothelial Cell Presentation and In Vivo Activity”, The Journal of Immunology, 2006, vol. 177, pp. 6991-6998.
Campanella, G S et al., “CXCR3 and Heparin Binding Sites of the Chemokine IP-10 (CXCL10)”, J of biol Chem, 2003, vol. 278, pp. 17066-17074.
Fadnes, A et al., “The proteoglycan repertoire of lymphoid cells”, Glycoconjugate journal, 2012, vol. 29, pp. 513-523.
Falsone, A et al., “Designing CXCL8-based decoy proteins with strong anti-inflammatory activity in vivo”, Bioscience reports, 2013, vol. 33, pp. 743-754.
Gattass, C R et al. “Constitutive Expression of Interferon y-inducible Protein 10 in Lymphoid Organs and Inducible Expression in T Cells and Thymocytes”, Journal of Experimental Medicine, 1994, vol. 179, pp. 1373-1378.
Gerlza, T et al., “A Combinatorial Approach to Biophysically Characterise Chemokine-Glycan Binding Affinities for Drug Development”, Molecules, 2014, vol. 19, pp. 10618-10634.
Gerlza, T et al. “Designing a mutant CCL2-HSA chimera with high glycosaminoglycan-binding affinity and selectivity”, Protein Engineering, Design and Selection, 2015, vol. 28, No. 8, pp. 231-240.
Gerlza, T et al. “Designing an improved T-cell mobilising CXCL10 mutant through enhanced GAG binding affinity”, Protein Engineering, Design and Selection, 202020, vol. 32, No. 8, pp. 367-373.
Handel, T M et al. “Regulation of Protein Function by Glycsaminoglycans—as Exemplified by Chemokines”, Annual review of biochemistry, 2005, vol. 74, pp. 385-410.
Hileman, R E et al. “Glycosaminoglycan-protein interactions: definition of consensus sites in glycosaminoglycan binding proteins”, Bioessays, 1998, vol. 20, pp. 156-167.
Hoogewerf, A J et al. “Glycosaminoglycans Mediate Cell Surface Oligomerization of Chemokines”, Biochemistry, 1997, vol. 36, pp. 13570-13578.
Jabeen, T et al. “Structure of mouse IP-10, a chemokine”, Acta Crystallographica Section D: Biological Crystallography, 2008, vol. 64, pp. 611-619.
Jiang, D et al. “Inhibition of pulmonary fibrosis in mice by CXCL10 requires glycosaminoglycan binding and syndecan-4”, The Journal of clinical investigation, 2010, vol. 120, pp. 2049-2057.

(Continued)

*Primary Examiner* — Ilia I Ouspenski
(74) *Attorney, Agent, or Firm* — Michael Fedrick; LOZA & LOZA, LLP

(57) ABSTRACT

Herein provided is a novel recombinant CXCL10 polypeptide with increased glycosaminoglycan (GAG) binding affinity compared to wild type CXCL10 and increasing T-cell mobilization and its use for preventing or treating inflammatory and immunological disorders and auto-immune diseases.

16 Claims, 8 Drawing Sheets

Figure 1:
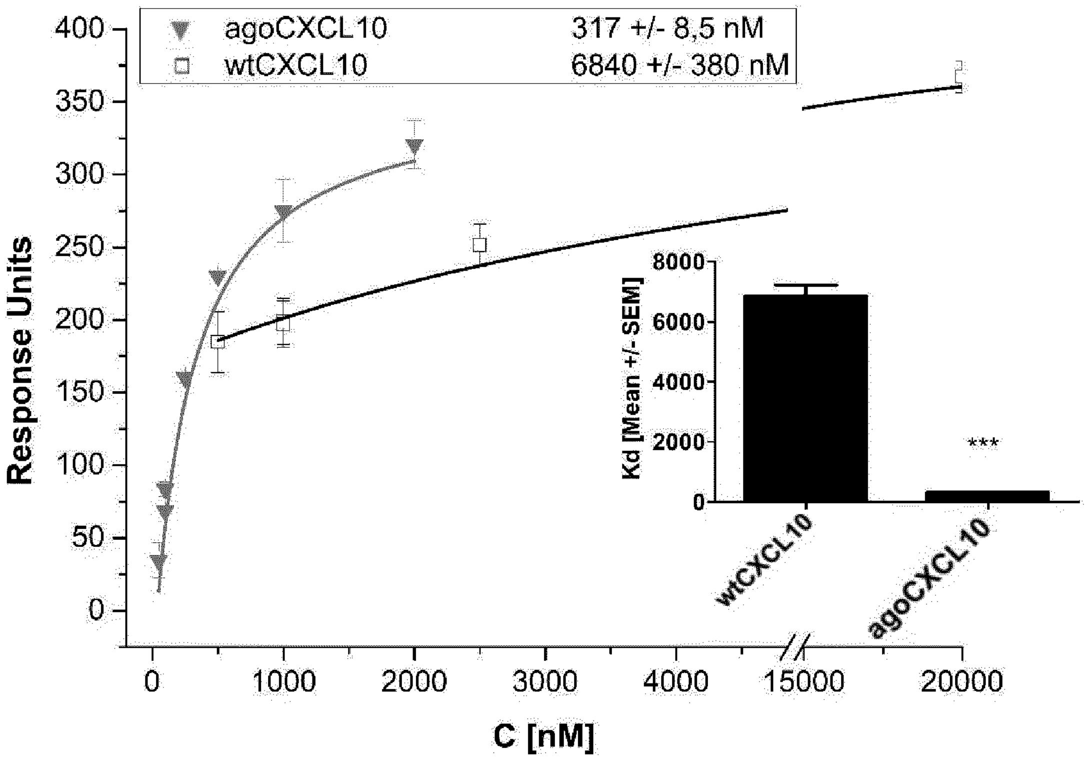

Specification includes a Sequence Listing.

(56) References Cited

OTHER PUBLICATIONS

Khan, I A et al. "IP-10 Is Critical for Effector T Cell Trafficking and Host Survival in Toxoplasma gondii Infection", Immunity, 2000, vol. 12, pp. 483-494.
Krieger, E et al. "Making Optimal Use of Empirical Energy Functions: Force-Field Parameterization in Crystal Space", Proteins, 2004, vol. 57, No. 4, pp. 678-683.
Krieger, E et al. "YASARA View—molecular graphics for all devices—from smartphones to workstations", Bioinformatics, 2014, vol. 30, No. 20, pp. 2981-2982.
Krieger, E et al. "New Ways to Boost Molecular Dynamics Simulations", J Comput Chem, 2015, vol. 36, pp. 996-1007.
Lindahl, U et al. "Pathophysiology of heparan sulphate: many diseases, few drugs", Journal of internal medicine, 2013, vol. 273, pp. 555-571.
Luster, A D et al., "The IP-10 Chemokine Binds to a Specific Cell Surface Heparan Sulfate Site Shared with Platelet Factor 4 and Inhibits Endothelial Cell Proliferation", Journal of experimental medicine, 1995, vol. 182, pp. 219-231.
Mach, F et al. "Differential expression of three T lymphocyte-activating CXC chemokines by human atheroma-associated cells", Journal of clinical investigation, 1999, vol. 104, No. 8, pp. 1041-1050.
Medoff, B D et al., "IFN-g-Inducible Protein 10 (CXCL10) Contributes to Airway Hyperreactivity and Airway Inflammation in a Mouse Model of Asthma", Journal of Immunology, 2002, vol. 168, pp. 5278-5286.
Moelants, E A et al. "Detection and Quantification of Citrullinated Chemokines", PLoS One, 2011, vol. 6, issue: 12, e28976, 8 pgs.
Moser, B et al. "Chemokines: role in inflammation and immune surveillance", Annals of the rheumatic diseases, 2004, vol. 63, pp. 84-89.
Murdoch, C et al. "Chemokine receptors and their role in inflammation and infectious diseases", Blood, 2000, vol. 95, No. 10, pp. 3032-3043.
Neel, N F et al. "Chemokine receptor internalization and intracellular trafficking", Cytokine & growth factor reviews, 2005, vol. 16, No. 6, pp. 637-658.
Parish, C R, "The role of heparan sulphate in inflammation", Nature Reviews Immunology, 2006, vol. 6, pp. 633-643.
Park, H J et al. "T cell migration in microchannels densely packed with T cells", Scientific reports, 2019, vol. 9;7198, 10 pgs.
Pignatti, P et al. "Role of the Chemokine Receptors CXCR3 and CCR4 in Human Pulmonary Fibrosis", American journal of respiratory and critical care medicine, 2006, vol. 173, pp. 310-317.
Proost, P et al. "The role of chemokines in inflammation", International Journal of Clinical and Laboratory Research, 1996, vol. 26, pp. 211-223.
Sørensen, T L et al. "Expression of specific chemokines and chemokine receptors in the central nervous system of multiple sclerosis patients", The Journal of clinical investigation, 1999, vol. 103, No. 6, pp. 807-815.
Saetta, M et al. "Increased Expression of the Chemokine Receptor CXCR3 and Its Ligand CXCL10 in Peripheral Airways of Smokers with Chronic Obstructive Pulmonary Disease", American journal of respiratory and critical care medicine, 2002, vol. 165, pp. 1404-1409.
Salanga, C L et al. "Chemokine Oligomerization and Interactions with Receptors and Glycosaminoglycans: The Role of Structural Dynamics in Function", Experimental cell research, 2011, vol. 317, No. 5, pp. 590-601.
Shimada, A et al. "The Role of the CXCL10/CXCR3 System in Type 1 Diabetes", The review of diabetic studies: RDS, 2009, vol. 6, No. 2, pp. 81-84.
Swaminathan, G J et al. "Crystal Structures of Oligomeric Forms of the IP-10/CXCL 10 Chemokine", Structure, 2003, vol. 11, pp. 521-532.
Tager, A M et al. "Inhibition of Pulmonary Fibrosis by the Chemokine IP-10/CXCL10", American journal of respiratory cell and molecular biology, 2004, vol. 31, pp. 395-404.
Trinker, M U et al. "Targeting chemokine-glycan interactions: the CellJammerR technology platform", Drug Discovery Today: Technologies, 2013, vol. 9, e253-e259.
Vives, R R et al. "A Kinetics and Modeling Study of RANTES(9-68) Binding to Heparin Reveals a Mechanism of Cooperative Oligomerization", Biochemistry, 2002, vol. 41, pp. 14779-14789.
Webb, L M et al. "Binding to heparan sulfate or heparin enhances neutrophil responses to interleukin", PNAS, 1993, vol. 90, pp. 7158-7162.
Weng, Y et al. "Binding and Functional Properties of Recombinant and Endogenous CXCR3 Chemokine Receptors*", Journal of biological chemistry, 1998, vol. 273, No. 29, pp. 18288-18291.
Yang, J et al. "The Angiostatic Activity of Interferon-Inducible Protein-10/CXCL10 in Human Melanoma Depends on Binding to CXCR3 but Not to Glycosaminoglycan", Molecular Therapy, 2004, vol. 9, No. 6, pp. 846-855.
International Search Report for corresponding International Patent Application No. PCT/EP2020/074068 dated Nov. 18, 2020; 5 pages.
Written Opinion for corresponding International Patent Application No. PCT/EP2020/074068 dated Nov. 18, 2020; 6 pages.
International Preliminary Report on Patentability for corresponding International Patent Application No. PCT/EP2020/074068 dated Mar. 1, 2022; 7 pages.

* cited by examiner

Fig. 5

Amino acid sequence of human wild type CXCL10:
VPLSRTVRCTCISISNQPVNPRSLEKLEIIPASQFCPRVEIIATMKKKGEKRCLNPESKAI
KNLLKAVSKERSKRSP (SEQ ID NO: 1).

Amino acid sequence of CXCL10 N20K (agoCXCL10)
VPLSRTVRCTCISISNQPVKPRSLEKLEIIPASQFCPRVEIIATMKKKGEKRCLNPESKAI
KNLLKAVSKERSKRSP (SEQ ID NO: 2).

Nucleotide sequence encoding wild type CXCL10:
ATGGTCCCGTTGTCCCGCACTGTCCGCTGTACTTGTATTTCGATTTCTAACCAACC
AGTCAATCCGCGTAGCCTGGAGAAGCTGGAAATCATCCCGGCCAGCCAGTTCTG
CCCGCGTGTGGAGATCATTGCGACCATGAAGAAGAAAGGTGAGAAACGTTGCCT
GAACCCGGAAAGCAAAGCGATCAAAAATCTGCTGAAGGCAGTTAGCAAAGAACGT
AGCAAGCGCAGCCCGTAA (SEQ ID NO: 4)

Nucleotide sequence encoding CXCL10 N20K (agoCXCL10):
ATGGTCCCGCTGTCCCGTACCGTTCGCTGCACTTGTATTTCTATTAGCAACCAGC
CGGTCAAGCCGCGCTCGCTGGAAAAACTGGAGATCATCCCGGCAAGCCAATTCT
GTCCGCGTGTTGAAATCATTGCCACGATGAAGAAGAAAGGTGAGAAGCGTTGCCT
GAACCCAGAAAGCAAAGCGATCAAAAATCTGTTGAAGGCGGTGAGCAAAGAGCG
CAGCAAGCGTAGCCCGTAA (SEQ ID NO: 5)

Amino acid sequence of CXCL10 Δ8 25K (ATG-N06)
CTCISISNQPVNPRSLKKLEIIPASQFCPRVEIIATMKKKGEKRCLNPESKAIKNLLKAVS
KERSKRSP (SEQ ID NO: 6)

Amino acid sequence of CXCL10 Δ8 VN20K (ATG-N07)
CTCISISNQPVKPRSLEKLEIIPASQFCPRVEIIATMKKKGEKRCLNPESKAIKNLLKAVS
KERSKRSP (SEQ ID NO: 7)

Amino acid sequence of CXCL10 Δ8 I12K (ATG-N08):
CTCKSISNQPVNPRSLEKLEIIPASQFCPRVEIIATMKKKGEKRCLNPESKAIKNLLKAV
SKERSKRSP (SEQ ID NO: 8)

Fig. 5 continued

Amino acid sequence of CXCL10 Δ8 I12K E25K (ATG-N09):
CTCKSISNQPVNPRSLKKLEIIPASQFCPRVEIIATMKKKGEKRCLNPESKAIKNLLKAV
SKERSKRSP (SEQ ID NO: 9)

Amino acid sequence of CXCL10 Δ8 I12K N20K E25K (ATG-N10):
CTCKSISNQPVKPRSLKKLEIIPASQFCPRVEIIATMKKKGEKRCLNPESKAIKNLLKAV
SKERSKRSP (SEQ ID NO: 10)

Amino acid sequence of CXCL10 Δ8 I12K I14K N20K E25K (ATG-N11):
CTCKSKSNQPVKPRSLKKLEIIPASQFCPRVEIIATMKKKGEKRCLNPESKAIKNLLKA
VSKERSKRSP (SEQ ID NO: 11)

Amino acid sequence of HAS-CXCL10 N20K (ATG-H06)
*VPLSRTVR*DAHKSEVAHRFKDLGEENFKALVLIAFAQYLQQAPFEDHVKLVNEVTEFA
KTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAA
FTECCQAADKAACLLPKLDELRDEGKASSAKQRLKCASLQKFGERAFKAWAVARLS
QRFPKAEFAEVSKLVTDLTKVHTECCHGDLLECADDRADLAKYICENQDSISSKLKEC
CEKPLLEKSHCIAEVENDEMPADLPSLAADFVESKDVCKNYAEAKDVFLGMFLYEYA
RRHPDYSVVLLLRLAKTYETTLEKCCAAADPHECYAKVFDEFKPLVEEPQNLIKQNCE
LFEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETFT
FHADICTLSEKERQIKKQTALVELVKHKPATKEQLKAVMDDFAAFVEKCCKADDKET
CFAEEGKKLVAASQAALGL*GGGGS*VPLSRTVRCTCISISNQPVKPRSLEKLEIIPASQF
CPRVEIIATMKKKGEKRCLNPESKAIKNLLKAVSKERSKRSP (SEQ ID NO: 12)

Fig. 5 continued

Amino acid sequence of modified human serum albumin

DAHKSEVAHRFKDLGEENFKALVLIAFAQYLQQAPFEDHVKLVNEVTEFAKTCVADES
AENCDKSLHTLFGDKLCTVATLRETYGEMADCCAKQEPERNECFLQHKDDNPNLPR
LVRPEVDVMCTAFHDNEETFLKKYLYEIARRHPYFYAPELLFFAKRYKAAFTECCQAA
DKAACLLPKLDELRDEGKASSAKQRLKCASLQKFGERAFKAWAVARLSQRFPKAEFA
EVSKLVTDLTKVHTECCHGDLLECADDRADLAKYICENQDSISSKLKECCEKPLLEKS
HCIAEVENDEMPADLPSLAADFVESKDVCKNYAEAKDVFLGMFLYEYARRHPDYSVV
LLLRLAKTYETTLEKCCAAADPHECYAKVFDEFKPLVEEPQNLIKQNCELFEQLGEYK
FQNALLVRYTKKVPQVSTPTLVEVSRNLGKVGSKCCKHPEAKRMPCAEDYLSVVLNQ
LCVLHEKTPVSDRVTKCCTESLVNRRPCFSALEVDETYVPKEFNAETFTFHADICTLS
EKERQIKKQTALVELVKHKPKATKEQLKAVMDDFAAFVEKCCKADDKETCFAEEGKK
LVAASQAALGL (SEQ ID NO: 19)

Figure 7:
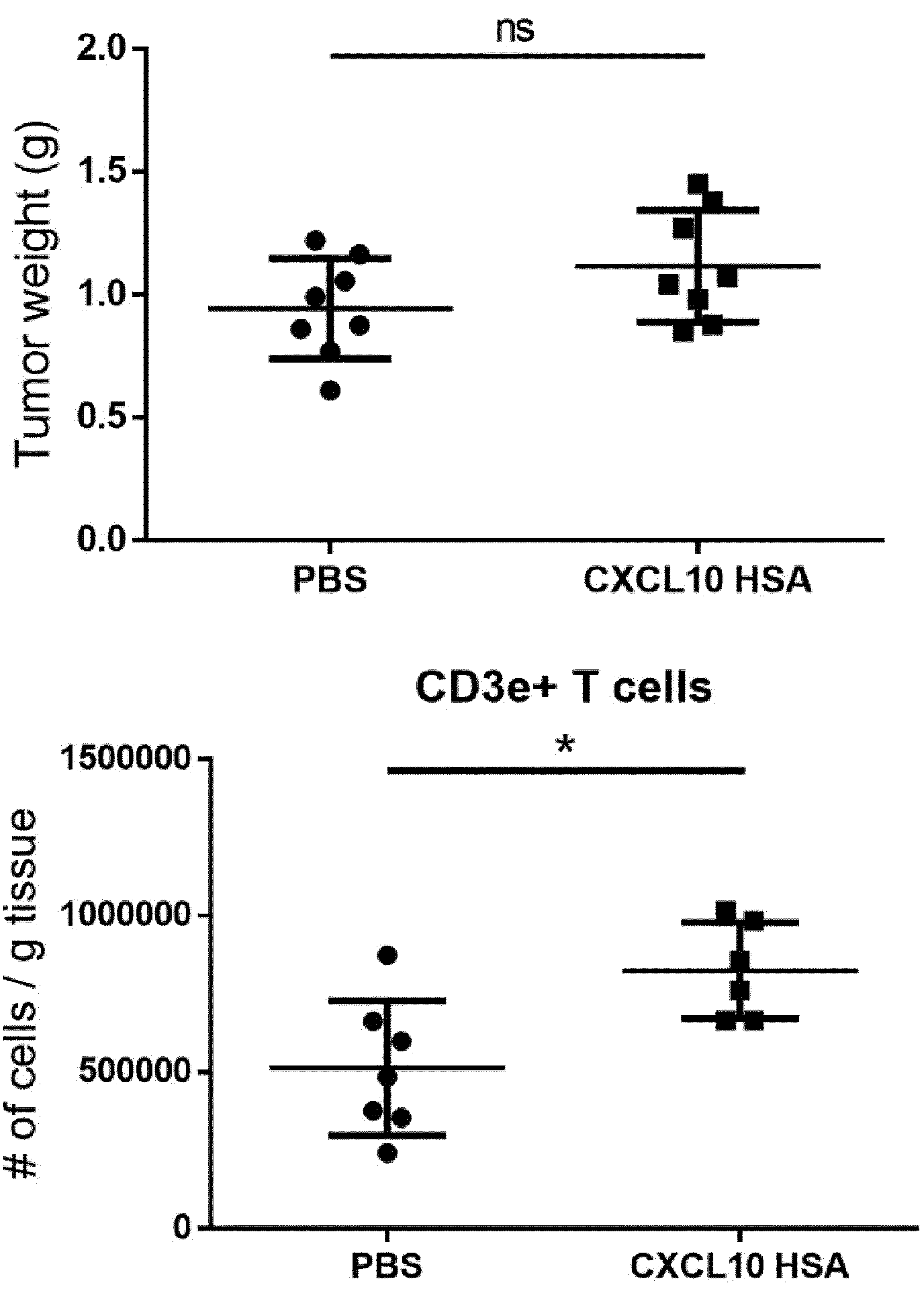

Fig. 7 continued
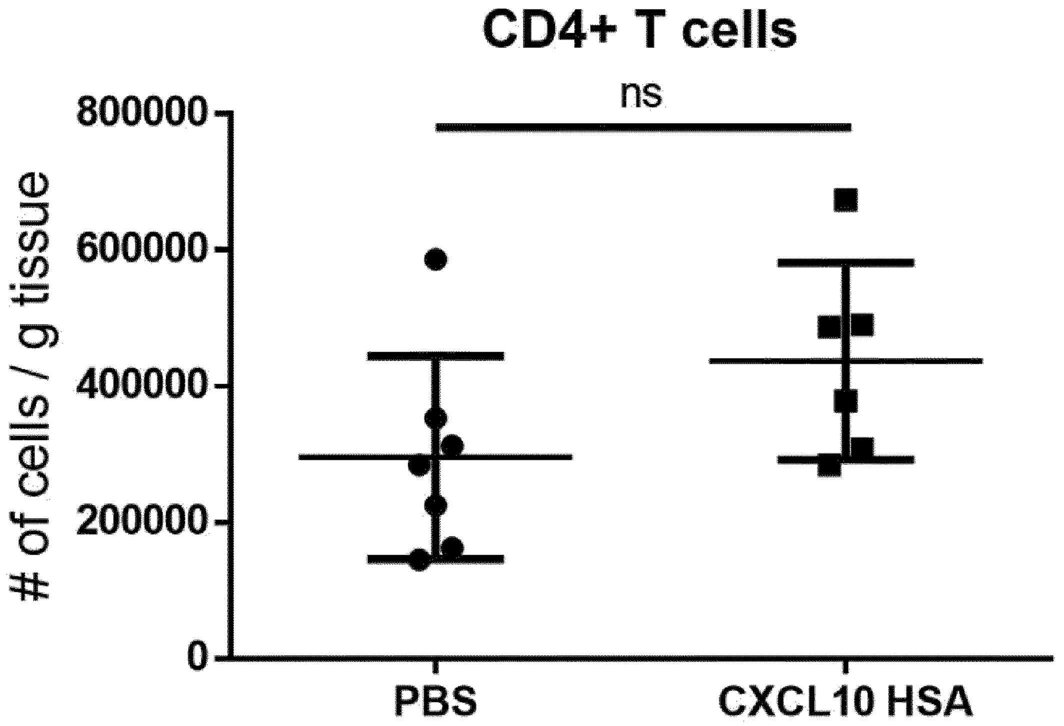
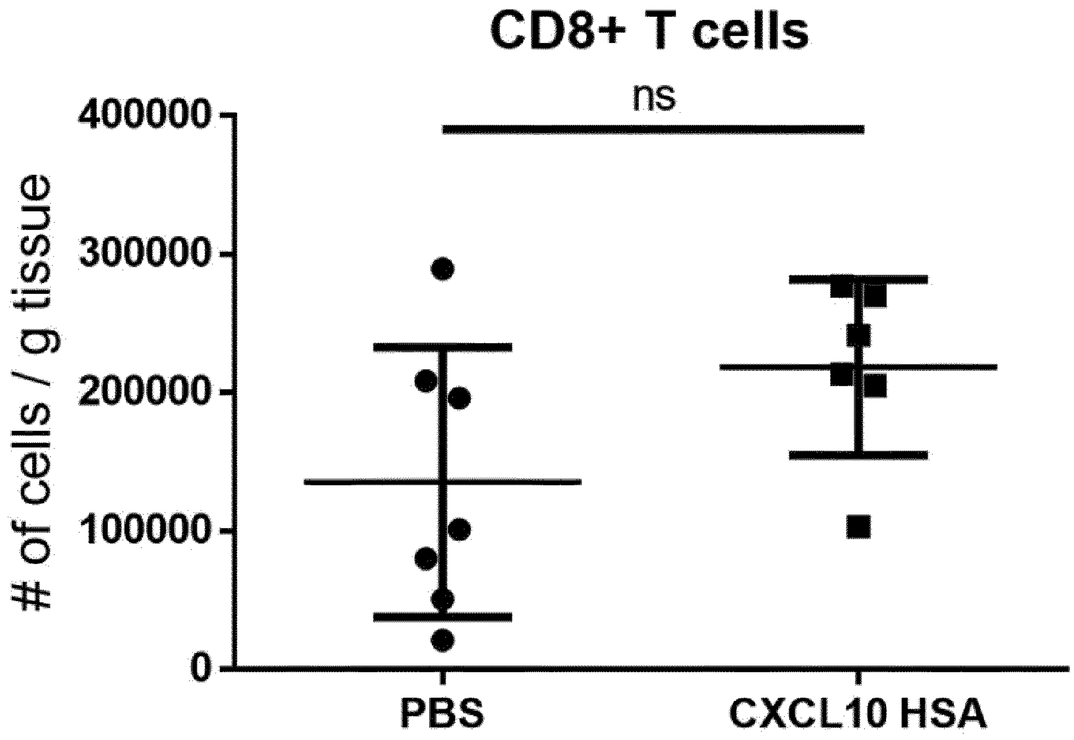

T-CELL MOBILIZING CXCL10 MUTANT WITH INCREASED GLYCOSAMINOGLYCAN BINDING AFFINITY

CROSS-REFERENCE TO RELATED APPLICATIONS

This application is the U.S. national stage of International Patent Application No. PCT/EP2020/074068, filed on Aug. 28, 2020 and entitled T-CELL MOBILIZING CXCL10 MUTANT WITH INCREASED GLYCOSAMINOGLYCAN BINDING AFFINITY, which claims the benefit of priority under 35 U.S.C. § 119 from European Patent Application No. 19194257.2, filed on Aug. 29, 2019. The disclosures of the foregoing applications are incorporated herein by reference in their entirety.

SEQUENCE LISTING

The entire content of a Sequence Listing titled "Sequence_Listing.txt," created on Aug. 4, 2025 and having a size of 19,739 bytes, which has been submitted in electronic form in connection with the present application, is hereby incorporated by reference herein in its entirety.

FIELD OF THE INVENTION

Herein provided is a novel recombinant CXCL10 polypeptide with increased glycosaminoglycan (GAG) binding affinity compared to wild type CXCL10 and having improved T-cell mobilization.

BACKGROUND OF THE INVENTION

Acute as well as chronic inflammatory events are characterized by infiltration of chemokine-activated leukocytes into the affected tissue. In orderto exert their functions, chemokines interact with their corresponding G protein-coupled receptors located on the leukocyte as well as with specific glycosaminoglycans (GAGs) presented in the terms of proteoglycans (PGs) on the surface of endothelial cells (Proost et al., 1996).

Chemokines are well-known key players in the immune system and in the process of angiogenesis and are also involved in pathological conditions like cancer. The interaction with cell-surface heparan sulfate proteoglycans is essential for their signalling via G-protein coupled receptors.

Chemokines stand for a large group of small cytokines. Their name is the result of their ability to induce chemotaxis or the directed movement of cells through a concentration gradient: chemotactic cytokines. The first chemokine to be characterized was Interleukin 8 in 1987. Nowadays there are about 50 known ligands, 18 standard receptors and 5 atypical receptors of the human chemokine family. In their monomeric form the molecular weight of the ligands ranges from 8-12 kDa, the receptors are about 40 kDa. It was found that chemokine genes tend to form specific clusters on certain chromosomal sites.

The chemokine Interferon gamma-induced protein 10 (CXCL10/IP-10), a member of the chemotactic cytokine family (chemokines), is released by a plethora of cells, including immune and metastatic cancer cells, following stimulation with interferon-gamma. It acts via its GPC receptor on T-cells attracting them to various target tissues. Glycosaminoglycans (GAGs) are regarded as co-receptors of chemokines, which enable the establishment of a chemotactic gradient for target cell migration.

CXCL10 is specifically released at sites of infection and inflammation but also injury and tissue growth by several different cell types including neutrophils, eosinophils, monocytes, epithelial, endothelial and stromal cells and keratinocytes thereby triggering the migration and infiltration of lymphocytes, dendritic cells, metastatic cells and stem cells. Besides its role during inflammation, CXCL10 is constitutively expressed in low levels in thymic, splenic and lymph node stroma making (Campanella et al., 2006, Moelants et al., 2011). As a member of the $ELR^-$ chemokines—CXC chemokines, which lack the distinct N-terminal Glu-Leu-Arg motif—it is also involved in the regulation of angiogenesis and has been shown to regulate progressive lung fibrosis (Falsone et al, 2013).

Posttranslational modifications of CXCL10 include the formation of disulfide bonds (position 30-57 and position 32-74), truncations of the C- and N-terminal end and citrullination (position 26) (Moelants et al, 2011).

Despite the diversity of functions and sequences of chemokines in general the tertiary structure of chemokines is highly conserved. Most of them have a similar fold characterized by three beta strands and one alpha helix but there is significant diversity in their oligomeric forms and propensity to oligomerise (Salanga and Handel, 2011).

The oligomerisation behavior of CXCL10 is still not completely understood though it is safe to claim, that oligomerization depends on the (local) concentration of chemokine and whether or not it is presented on certain biological structures like cell surface proteoglycans (PGs). It has been demonstrated that chemokines can oligomerize on proteoglycans—more precisely the GAG part of the proteoglycan—at physiologic, low nanomolar concentrations, where they would normally be present as monomers (Hoogewerf et al., 1997, Vives et al., 2002). Oligomerization of CXCL10 is required for the presentation on endothelial cells and the subsequent transendothelial migration, an essential step for lymphocyte recruitment in vivo (Campanella et al, 2006). CXCL10 binds to the receptor CXCR3, which is expressed on activated T and B cells, NK cells, monocytes, macrophages and dendritic cells and plays an important role in Th1-type inflammatory diseases, especially lung associated inflammatory diseases like COPD, asthma and pulmonary fibrosis (Khan et al., 2000, Murdoch and Finn, 2000). Chemokine receptors share a common seven-transmembrane structure and couple to G proteins for signal transduction making them members of the family of G protein-coupled receptors (GPCRs). Experiments have indicated that these receptors typically require G-proteins of the $G_i$-type for signal transduction (Moser and Willimann, 2004).

Other CXC chemokines which are known to additionally interact with the CXOR3 receptor are CXCL9 (MIG: Monokine induced by Gamma-Interferon, Small Inducible Cytokine Subfamily B Member 9, SCYB9) and CXCL11 (1-TAC: Interferon-inducible T-cell alpha chemoattractant; IP-9: Interferon gamma-induced protein 9, SCYB11) which shows one of the most distinct features of chemokine receptors and chemokines: their binding promiscuity (Campanella et at, 2006, Moelants et al, 2011).

CXCL11 has the highest binding affinity towards CXCR3, whereas CXCL9 and CXCL10 bind with a lower and similar affinity. Interestingly, also other CC-chemokines like CCL11 (eotaxin) and CCL13 (MCP-4) bind to CXCR3 but with a much lower affinity and without activating the receptor (Weng et al., 1998).

Glycosaminoglycans (GAGs) are linear, heterogeneous and highly sulfated polysaccharides consisting of repeating disaccharide units. These units (except for keratan sulfate) consist of an amino sugar (N-acetylglucosamine or N-acetylgalactosamine) and an uronic acid (glucuronic acid or iduronic acid) or galactose (Handel et al, 2005). The major classes of GAGs are distinguished by the composition of their disaccharide units as well as the geometry of their glycosidic linkage. The GAGs themselves also vary in chain length, grade of acetylation and grade of N- and O-sulfation. The different members of the GAG superfamily are heparin, heparan sulfate, chondroitin sulfate, dermatan sulfate, keratan sulfate and hyaluronic acid. These GAGs are usually covalently attached to core proteins thus forming the proteoglycans (PGs) which are located on the cell surface of virtually all eukaryotic cells and in the extracellular matrix constituting the glycocalyx (Handel at al, 2005). Co-receptors for CXCL10 are most probably heparan sulfate proteoglycans (HSPGs) (Luster et al., 1995), which are the most ubiquitous PGs that are expressed on cell surfaces and comprise 50-90% of all PGs of endothelial cells (Parish, 2006). The two major families of HSPGs, namely Syndecans (SDC 1-4) and Glypicans (GPCC 1-6), were found to be involved in many pathophysiological processes which makes them interesting therapeutic targets (Lindahl and Kjellén, 2013, Luster et al., 1995).

CXCL10 is considered a late stage chemokine, which means that any therapeutic approach targeting CXCL10 will address chronic rather than acute inflammatory diseases. The effects of CXCL10 in vivo are complex, diverse and probably not completely understood yet. In addition to its role as a proinflammatory chemokine, CXCL10 occurs in lymphoid organs and may participate in T cell effector function and perhaps T cell development (Gattass et at, 1994). An altered expression level of CXCL10 was discovered in many inflammatory diseases like atherosclerosis (Mach at al., 1999), multiple sclerosis (Sørensen et al., 1999), type 1 diabetes (Shimada et al., 2009), lung associated diseases like chronic obstructive pulmonary disease (COPD) (Saetta et al., 2002) and allergic asthma/allergic pulmonary inflammation (Medoff et at, 2002) and many more.

WO2005054285A1 and Adage et al., 2012 describe the generation of dominant-negative chemokine mutants with increased GAG-binding affinity but combined with knocked-out GPC receptor activity which were found to be potent inhibitors of leukocyte mobilization in vitro and in vivo.

Interfering with the chemokine/chemokine receptor network is a pharmacologically exploitable way to treat or cure inflammatory diseases even though the complexity of this network and especially the receptor promiscuity are reasons which contribute to the failure of so many agents that target chemokines (Trinker and Kungl, 2013). In order to exert their functions, chemokines—similar to other biomolecules like growth factors—have to bind to glycosaminoglycans. This co-receptor is often neglected in designing new pharmacological substances targeting chemokines. A typical biopharmaceutical approach of blocking chemokine-receptor signaling is the design of antibodies, which mask chemokines, but several antibodies failed in clinical studies due to their incapability to bind to chemokinas, which are presented on glycosaminoglycan sites on the endothelium (Bernfield et al., 1999, Handel et al., 2005).

T cells migrate diverse microenvironments of the body to mount antigen-specific immune responses. T cell migration is essential for T cell responses; it allows for the detection of cognate antigen at the surface of antigen-presenting cells and for interactions with other cells involved in the immune response. Rapid trafficking to specific organs/tissues and robust motility within diverse tissue microenvironments are critical characteristics of T cells as orchestrators of antigen specific immune responses. For immune surveillance, T cells circulate secondary lymphoid organs such as spleens and lymph nodes (LNs) where information of potentially harmful antigens is collected and presented by antigen presenting cells (APCs) (Park H J and Doh J, Scientific reports, 9, 7198, 2019).

T cell activation by T cell-APC interactions in secondary lymphoid organs is a key event for the initiation of antigen-specific immune responses. Activated T cells undergo clonal expansion, and traffic to effector sites to mount antigen-specific immune responses.

In view of above, there is a high demand for providing compounds which can mobilize T-cells.

SUMMARY OF THE INVENTION

It is an object of the invention to provide an improved cytokine which has increased GAG binding affinity while T-cell mobilizing capability is preserved.

The object is solved by the subject matter of the present invention described herein.

Herein provided is a modified cytokine, CXCL10, which has improved GAG binding affinity and can act as T-cell mobiliser.

A human CXCL10 was developed with improved T-cell mobilization by implementing a mutation into the protein which leads to a higher GAG binding affinity compared to wild type CXCL10.

Surprisingly, in order to test the improved characteristics of the modified CXCL10, this mutation not only increased T-cell migration in a migration assay, the mutant intensified T-cell chemotaxis also in a Boyden chamber set-up thereby indicating a strong role of T-cell-localized GAGs on leukocyte migration. A CXCL10 mutant with increased GAG-binding affinity could therefore potentially serve as a T-cell mobiliser in pathological conditions where the immune surveillance of the target tissue is impaired, as is the case for e.g. most solid tumors.

According to the invention, there is provided a recombinant CXCL10 polypeptide with increased glycosaminoglycan (GAG) binding affinity compared to wild type CXCL10, comprising one or more amino acid substitutions at any one of positions 12, 14, 20 or 25 with reference to SEQ ID NO: 1 or any combinations thereof, specifically the one or more substitution is Arginine (R) or Lysine (K), more specifically it is K.

Specifically, the recombinant CXCL10 polypeptide described herein is comprising one single substitution, specifically N at position 20 is substituted by K.

According to a specific embodiment, the recombinant CXCL10 polypeptide described herein comprises at least 90%, 91%, 92%, 93%, 94%, 95%, 96%, 97%, 98%, specifically at least 99% sequence identity with SEQ ID NO: 1.

According to a specific embodiment, the recombinant CXCL10 polypeptide provided herein comprises the amino acid sequence of the formula:

VPLSRTVRCTC(X1)S(X2)SNQPV(X3)PRSL(X4) KLEIIPASQFCPRVEIIATMKK KG EKROLNPESKAIKNLLKAVSKERSKRSP (SEQ ID NO: 3), wherein X1 is I, K, or R, wherein X2 is I, K, or Ra, wherein X3 is N, K, or R and wherein X4 is E, K, or R.

Specifically, the recombinant CXCL10 polypeptide described herein comprises an N-terminal deletion of 1, 2, 3, 4, 5, 6, 7, or 8 amino acids.

According to a specific embodiment, the recombinant CXCL10 polypeptide comprises SEQ ID NO: 2.

According to a further specific embodiment, the recombinant CXCL10 polypeptide consists of SEQ ID NO: 2.

According to an alternative embodiment, the recombinant CXCL10 polypeptide described herein comprises at least 90%, 91%, 92%, 93%, 94%, 95%, 96%, 97%, 98%, specifically at least 99% sequence identity with any one of SEQ ID NOs: 6-11.

Specifically, the recombinant CXCL10 polypeptide comprises one or more tag sequences at its C- or N-terminus, specifically selected from selected from human serum albumin, and non-reactive Fc parts of antibodies. More specifically, human serum albumin (HSA) is linked to the N-terminus of the CXCL10 polypeptide described herein, optionally further comprising a linker sequence.

More specifically, the recombinant CXCL10 polypeptide comprises SEQ ID NO: 12.

According to an embodiment, the recombinant CXCL10 polypeptide provided herein has at least 2-fold, specifically at least 5-fold, more specifically at least 10-fold increased affinity for GAG compared to wild type CXCL10 of SEQ ID NO: 1.

Specifically, the recombinant CXCL10 polypeptide described herein is provided for use in preventing or treating a disease selected from the group consisting of inflammatory and -immunological disorders, specifically for the treatment of T-cell related immunological diseases, more specifically for the treatment of immune-oncological disorders like solid tumors, metastasis formation, as well as for auto-immune diseases.

More specifically, a method for treating a disease selected from the group consisting of inflammatory and immunological disorders, specifically for the treatment of T-cell related immunological diseases, more specifically for the treatment of immune-oncological disorders like solid tumors, metastasis formation, as well as for auto-immune diseases in a subject is provided.

Further provided is an isolated polynucleic acid molecule that codes for a polypeptide provided herein.

Further provided is a vector that comprises an isolated DNA molecule described herein.

Further provided is a recombinant non-human cell that it is transfected with a vector according described herein.

In a further embodiment, a pharmaceutical composition is provided, comprising the recombinant CXCL10 polypeptide provided herein, or a polynucleic acid molecule provided herein or a vector provided herein, and a pharmaceutically acceptable carrier.

Specifically, herein provided is the use of the recombinant CXCL10 polypeptide described herein for in vitro mobilizing T-cells.

FIGURES

FIG. 1: Binding isotherms of wtCXCL10 and agoCXCL10 (CXCL10 N20K) binding to HS as determined by surface plasmon resonance. In the insert the respective Kd values are shown.

Figure 2:
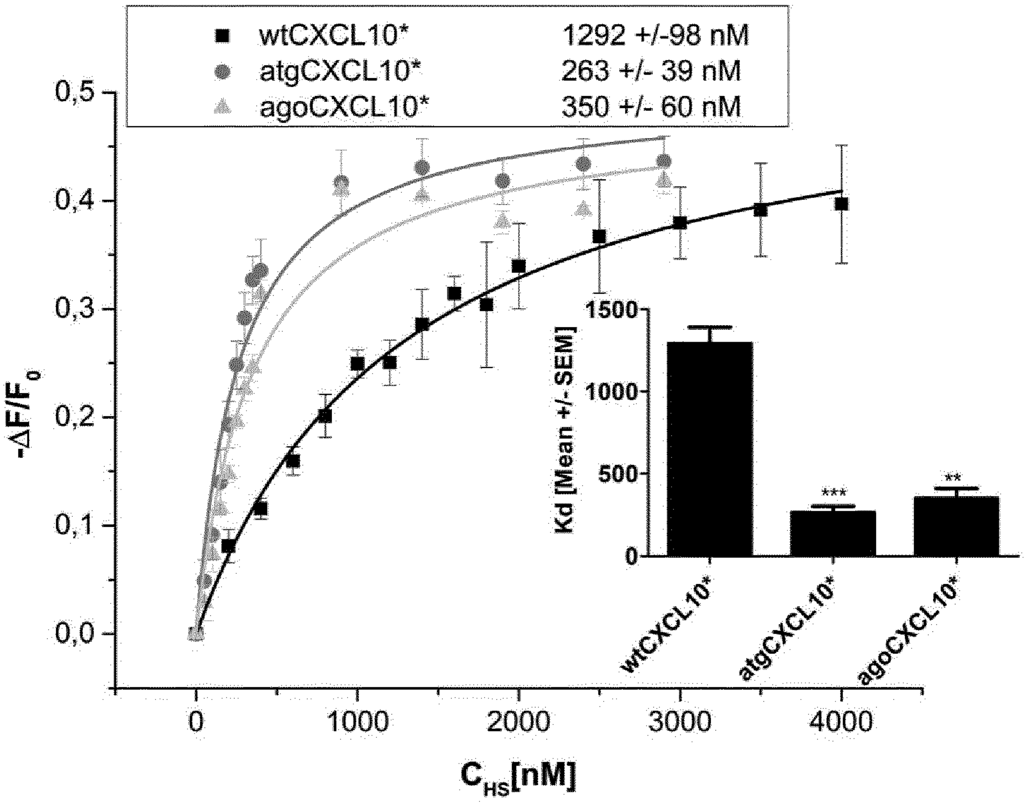

FIG. 2: Binding isotherms of wtCXCL10*, agoCXCL10* and atgCXCL10* (CXCL10 Δ8 V19W N20K) binding to HS as determined by isothermal fluorescence titration. In the insert the respective Kd values are shown.

Figure 3:
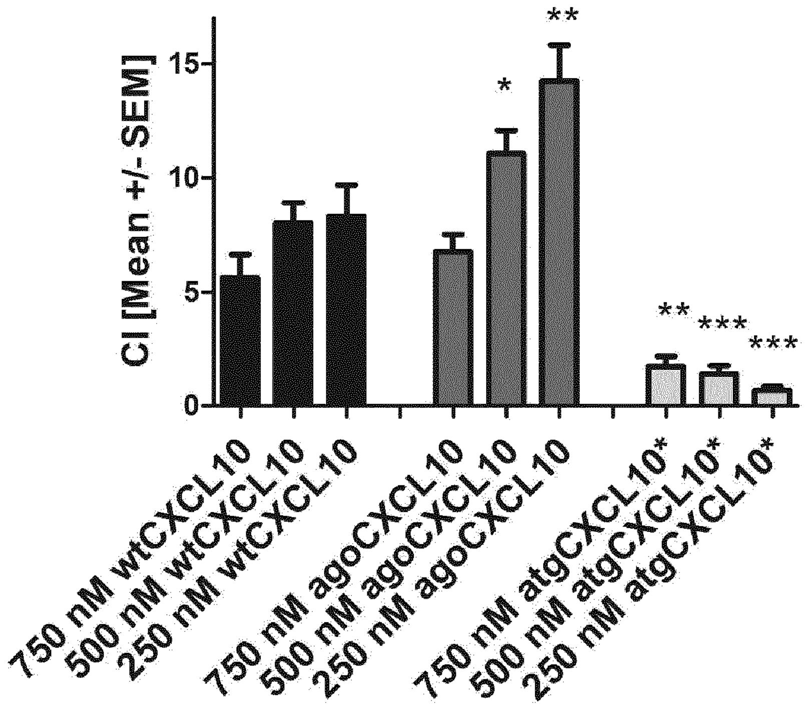

FIG. 3: Chemotactic activity of CXCL10, agoCXCL10 and atgCXCL10 on stimulated T-cells using Boyden chamber assay. The chemotactic index (CI) represents the mean cell number of migrated cells divided through the mean cell number of background migration. *$p<0.05$, $p<0.01$, *$p<0.001$ was considered as statistically significant.

Figure 4:
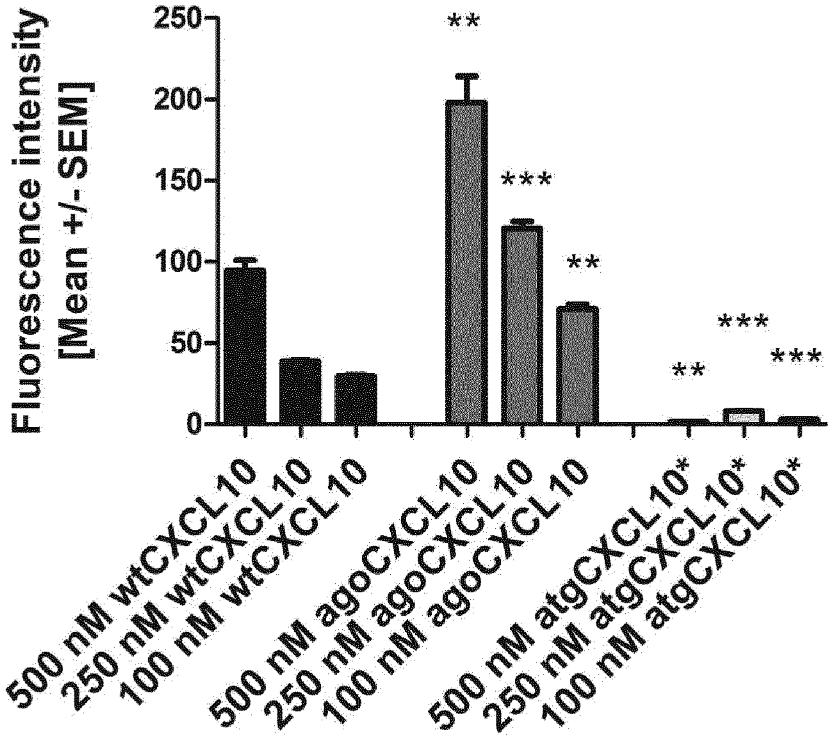

FIG. 4: in vitro transendothelial migration of T-cells upon stimulation with CXCL10, agoCXCL10 and atgCXCL10 on stimulated T-cells using Boyden chamber assay. The migration was background corrected and data sets were compared to their respective wild-type concentration using Ttest. *$p<0.05$, $p<0.01$ *$p<0.001$ was considered as statistically significant.

FIG. 5: Amino acid and nucleotide sequences of wild type and mutant CXCL10.

Figure 6:
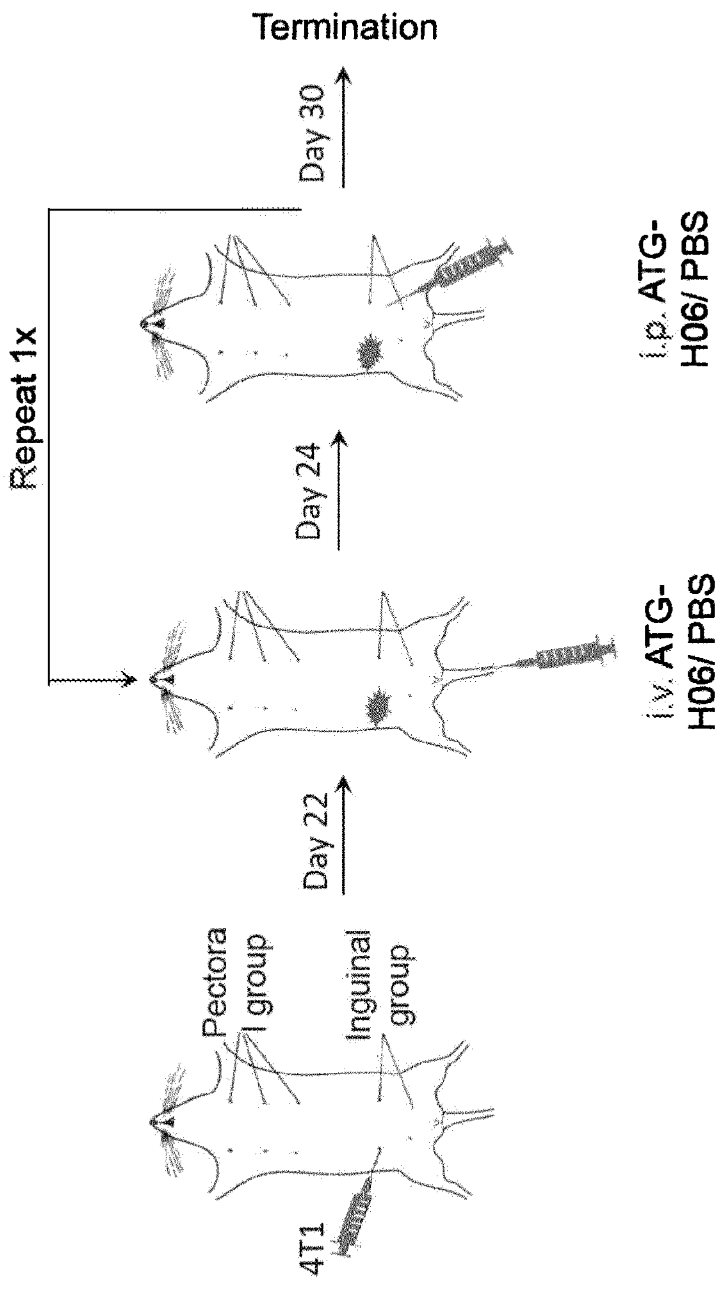

FIG. 6: In vivo systemic treatment—4T1 m.f.p. model. In vivo 4T1 mammary fat pad model: 4T1 cells (breast cancer) were injected into the mammary fat pad of balb/c mice. After establishment of the tumor mice were treated systemically with CXCL10-HSA (50 ug/injection) or PBS intravenously or intraperitoneally.

FIG. 7: FACS analysis of 4T1 systemic treatment model—TUMOR: no significant difference was found in tumor weight. However, an increase in CD3e+ T cells was found in the ATG-H06 treated mice within the tumor. Also trends of more CD4/CD8a T cells are found in ATG-H06 treated mice.

DETAILED DESCRIPTION

Unless indicated or defined otherwise, all terms used herein have their usual meaning in the art, which will be clear to the skilled person. Reference is for example made to standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions, Garland Science, New York, 2001). Sambrook et al, "Molecular Cloning: A Laboratory Manual" (4th Ed.), Vols. 1-3, Cold Spring Harbor Laboratory Press (2012); Krebs et al., "Lewin's Genes X1", Jones & Bartlett Learning, (2017), and Murphy & Weaver, "Janeway's Immunobiology" (9th Ed., or more recent editions), Taylor & Francis Inc, 2017.

The subject matter of the claims specifically refers to artificial products or methods employing or producing such artificial products, which may be variants of native (wild-type) products. Though there can be a certain degree of sequence identity to the native structure, it is well understood that the materials, methods and uses of the invention, e.g., specifically referring to isolated nucleic acid sequences, amino acid sequences, fusion constructs, expression constructs, transformed host cells and modified proteins including enzymes, are "man-made" or synthetic, and are therefore not considered as a result of "laws of nature".

The terms "comprise" "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein, amino acids refer to twenty naturally occurring amino acids encoded by sixty-one triplet codons.

These 20 amino acids can be split into those that have neutral charges, positive charges, and negative charges.

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gin, Q) polar, neutral;
Glycine: (Gly, G) nonpolar, neutral;
Isoleucine: (lie, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:

Arginine: (Arg, R) polar, positive; and
Lysine: (Lys, K) polar, positive.

The "negatively" charged amino acids are:

Aspartic acid: (Asp, D) polar, negative; and
Glutamic acid: (Glu, E) polar, negative.

The term "sequence identity" as used herein is understood as the relatedness between two amino acid sequences or between two nucleotide sequences and described by the degree of sequence identity or sequence complementarity. The sequence identity of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or polynucleotides by detecting excess similarity, and statistically significant similarity that reflects common ancestry. Homologues may encompass orthologues, which are herein understood as the same protein in different organisms, e.g., variants of such protein, CXCL10, in different different organisms or species.

"Percent (%) identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences can be determined using the NCBI, specifically NCBI BLAST+2.9.0 program version (Apr-02-2019).

"Percent (%) identity" with respect to a nucleotide sequence e.g., of a nucleic acid molecule or a part thereof, in particular a coding DNA sequence, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

Optimal alignment may be determined with the use of any suitable algorithm tor aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomies.org.cn), and Maq (available at maq.sourceforge.net).

The term "CXCL10 polypeptide" refers to CXCL10 also known as Interferon gamma-induced protein 10 (IP-10) or small-inducible cytokine B10.

The terms "CXCL10 polypeptide with increased GAG binding affinity", "variant of CXCL10" and "CXCL10 mutant" means any fragment or derivative or variant of a CXCL10 polypeptide comprising the amino acid modifications according to the invention and still having the chemokine's remaining properties.

The recombinant CXCL10 polypeptide variant described herein has increased glycosaminoglycan (GAG) binding affinity compared to wild type CXCL10 while still preserving other chemokine properties, specifically comprising one or more amino acid substitutions at least at any one of positions 12, 14, 20 and/or 25 with reference to SEQ ID NO: 1 or any combinations thereof.

Variants or mutants of CXCL10 as described herein comprise any of positions 12, 14, 20 or 25 with reference to SEQ ID NO: 1 as single substitution or any combinations of said substitutions.

The positions are substituted by Lysine or Arginine, more specifically it is Lysine.

Specifically, the CXCL10 mutants comprise substitutions E25K; N20K; I12K; I12K and E25K; I12K, N20K and E25K: I12K, 114K, N20K and E25K: optionally further comprising a deletion of 8 N-terminal amino acids and further optionally comprising V19W for introducing a fluorophore. Alternatively, the CXCL10 mutants comprise substitutions E25R; N20R: I12R; I12R and E25R; I12R, N20R and E25R; I12R, I14R, N20R and E25R; optionally further comprising a deletion of 8 N-terminal amino acids and further optionally comprising V19W for introducing a fluorophore.

Specifically, the CXCL10 comprises a substitution of K or R at position 20 of SEQ ID NO:1, more specifically it is K.

The recombinant CXCL10 polypeptide may comprise some sequence variation but at least 95%, 96%, 97%, 98%, 99% sequence identity with SEQ ID NO: 1 as long as it is a functional active variant of wild type CXCL10 with respect to T-cell mobilization with a chemotactic index at least as good as the wild type.

Specifically, the recombinant CXCL10 polypeptide comprises or consists of SEQ ID NO: 2 or any of SEQ ID NOs: 6-12.

The terms "polypeptide", "peptide", and "protein", can be used interchangeably herein and may refer to a polymeric form of amino acids of any length, which can include naturally-occurring amino acids, coded and non-coded amino acids, chemically or biochemically modified, derivatized, or designer amino acids, amino acid analogs, peptidomimetics, and polypeptides having modified, cyclic, or bicyclic peptide backbones. The term also includes single chain proteins as well as multimers.

The term "functional variant" or "functionally active variant" also includes naturally occurring allelic variants, as well as mutants or any other non-naturally occurring variants. As is known in the art, an allelic variant is an alternate form of a nucleic acid or peptide that is characterized as having a substitution, deletion, or addition of one or nucleotides or more amino acids that does essentially not alter the biological function of the nucleic acid or polypeptide.

Specifically, the recombinant CXCL10 polypeptide comprises the amino acid sequence of SEQ ID NO: 3

```
VPLSRTVRCTC(X1)S(X2)SNQPV(X3)PRSL(X4)KLEIIPASQFCPR

VEIIATMKKKG EKRCLNPESKAIKNLLKAVSKERSKRSP,
```

wherein X1 is I or K or R, specifically it is K,
wherein X2 is I or K or R, specifically it is K,
wherein X3 is N or K, or R, specifically it is K, and
wherein X4 is E or K or R, specifically it is K.

Additionally, the CXCL10 polypeptide can comprise an N-terminal deletion of 1, 2, 3, 4, 5, 6, 7, or 8 amino acids.

Merely for determining GAG binding affinity, the CXCL10 described herein comprises further substitutions for introducing fluorophores such as conformationally sensitive fluorophores. As an example, valine at position 19 of SEQ ID NO: 1 is replaced by tryptophan.

The CXCL10 polypeptides described herein may further provide one or more N-terminal or C-terminal tag sequences. Such tag sequence may comprise any number of amino acids of more than 2, 5 or 10 amino acids and up to 20, 50, 100, 200 or more amino acids. Specifically, tag sequences used herein may be any tag sequence known to the person skilled in the art. Specifically, tag sequences used herein are selected from pharmacological improvement tags, affinity tags, solubility enhancement tags or monitoring tags. Specifically, any tag with any function known in the art can be fused to CXCL10. Of particular interest for agonistic mutants are peptide tags which resemble the CXCR3 activation domain. As an example, said CXCR3 activation tag may comprise the N-terminal CXCL10 sequence VPLSRTVR (SEQ ID NO: 18) or a fragment thereof comprising 2, 3, 4, 5, 6 or 7 amino acids.

Pharmacological improvement tags are amino acid sequences that provide better in vivo pharmacological characteristics to the mutant protein by increasing its molecular weight and thus stability, bioavailability, serum half-life and drug exposure. According to a specific embodiment, pharmacological improvement tag sequences used herein are selected from human serum albumin, non-reactive Fc parts of antibodies, or any other tag known to be useful for the efficient improvement of pharmacological characteristics of a protein it is fused to.

Specifically, the tag is human serum albumin (HSA).

According to a specific embodiment, the HSA sequence comprises an amino acid substation at position 34, specifically alanine, to prevent dimerization.

Specifically, the tag is a CXCR3 activation tag.

More specifically, the CXCL10 variant may comprise from the N-terminus a CXCR3 tag, a HSA sequence, a further CXCR3 tag and the modified CXCL10 sequence comprising one or more amino acid substitutions at positions 12, 14, 20 and/or 25 of SEQ ID NO: 1 or any combinations thereof. Specifically, the CXCL10 variant comprises a single substitution at position 20.

According to a specific embodiment, the protein tag described herein further comprises one or more linker sequences comprising one or more amino acid residues. Specifically, said linker sequence comprises 1, 2, 3, 4, 5, 6, 7, 8, 9, 10, 11, 12, 13, 14, 15, 16, 17, 18, 19 or 20 or more amino acid residues. Specifically, the linker can comprise more than 20 or 30 or even more amino acids, as long as the caspase retains its functional activity as described herein. Specifically, the one or more amino acid residues of the linker sequence are any of the naturally occurring amino acids or derivatives thereof, preferably selected from the group consisting of G, S, T, N, A. Specifically, the linker sequence comprises glycine, alanine and/or serine residues. Specifically, the linker comprises at least one glycine and serine residue, more specifically the linker is GS, GGGG5 (SEQ ID NO: 13), GSG (SEQ ID NO: 14), GGSGG (SEQ ID NO: 15), GSGSGSG (SEQ ID NO: 16) and/or GSAGSAAGSG (SEQ ID NO: 17). Specifically, the linker sequences can be repeated 1, 2 or 3 times.

According to a further specific embodiment, the monitoring tag sequence used herein is m-Cherry, GFP or f-Actin or any other tag useful for detection or quantification of the CXCL10 during production of the CXCL10 including fermentation, isolation and purification by simple in-situ, inline online or atline detectors, like UV, IR, Raman, Fluorescence and the like.

The CXCL10 mutant described herein specifically shows increased GAG binding affinity, specifically GAG binding affinity is increased at least 2-fold, 3-fold, 4-fold, 5-fold, 6-fold, 7-fold, 8-fold, 9-fold, 10-fold, or more compared to wild type CXCL10.

A further aspect of the present invention is an isolated polynucleic acid molecule which codes for the inventive polypeptide as described herein. The polynucleic acid may be DNA or RNA. Specifically, the polynucleotide sequence is SEQ ID NO: 4 or SEQ ID NO: 5. Thereby the modifications which lead to the CXCL10 mutant polypeptide described herein are carried out on DNA or RNA level. This inventive isolated polynucleic acid molecule is suitable for diagnostic methods as well as gene therapy and the production of inventive CXCL10 mutant polypeptide on a large scale.

The term "expression" is understood in the following way. Nucleic acid molecules containing a desired coding sequence of an expression product such as e.g., the CXCL10 as described herein, may be used for expression purposes. Such nucleic acid molecules are specifically referred to as "isolated nucleic acid molecule" or "isolated nucleotide sequence". Hosts transformed or transfected with these sequences are capable of producing the encoded proteins. In order to effect transformation, the expression system may be included in a vector: however, the relevant DNA may also be integrated into the host chromosome. Specifically, the term refers to a host cell and compatible vector under suitable conditions, e.g., for the expression of a protein coded for by foreign DNA carried by the vector and introduced to the host cell.

Coding DNA is a DNA sequence that encodes a particular amino acid sequence for a particular polypeptide or protein. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors often include one or more replication systems for cloning or expression, one or more markers for selection in the host, e.g., antibiotic resistance, one or more nuclear localization signals (NLS) and one or more expression cassettes.

"Expression vectors" or "vectors" as used herein are defined as DNA sequences that are required for the transcription of cloned recombinant nucleotide sequences, i.e. of recombinant genes and the translation of their mRNA in a suitable host organism. To obtain expression, a sequence encoding a desired expression product, such e.g. the CXCL10 described herein, is typically cloned into an expression vector that contains a promoter to direct transcription. Suitable bacterial and eukaryotic promoters are well known in the art. The promoter used to direct expression of a nucleic acid depends on the particular application. For example, a strong constitutive promoter is typically used for expression and purification of recombinant proteins. In contrast, when the expression product is to be administered in vivo for gene regulation, either a constitutive or an inducible promoter can be used, depending on the particular use of the expression product. In addition, a preferred promoter for administration can be a weak promoter. The promoter can also include elements that are responsive to transactivation, e.g., hypoxia response elements, Gal4 response elements and lac repressor response elements. Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together.

An "expression cassette" refers to a DNA coding sequence or segment of DNA coding for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence.

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al.).

As used herein the term "host cell" refers to one or more cells which can be used in the methods described herein. Typically, the term refers to viable cells, capable of growing in a cell culture, into which a heterologous nucleic acid sequence or amino acid sequence is introduced. Specifically, the host cells are selected from the group consisting of bacterial cells, yeast cells, insect cells, mammalian cells and plant cells. Mammalian cells used in accordance with the present disclosure typically are human or rodent cells, such as mouse, rat or hamster cells, such as for example Chinese Hamster Ovary (CHO) cells.

Any host cell can be used for expressing the CXCL10 mutant described herein. Specifically, the non-human living host cells are prokaryotic or eukaryotic cells. Common cells that serve as hosts for expression of recombinant genes are e.g. *Escherichia coli, Bacillus* species, *Streptomyces* species, Yeast strains such as *Saccharomyces, Schizosaccharomyces, Pichia, Kluyveromyces* or *Hansenula* strains, insect cells, mammalian cell lines, plant cells. Expression hosts can also be at the level of a multicellular organism such as transgenic plants, sheep, goat, cow, chicken and rabbit, whereby the product can be isolated either from organs or from body fluids such as milk, blood or eggs. Alternatively, the gene can be translated into protein using cell free translation systems, possibly coupled to an in vitro transcription system. These systems provide all steps necessary to obtain protein from DNA by supplying the necessary enzymes and substrates in an in vitro reaction. In principle, any living cell or organism can provide the necessary enzymes for this process and extraction protocols for obtaining such enzyme systems are known in the art. Common systems used for in vitro transcription/translation are extracts or lysates from reticulocytes, wheat germ or *E. coli.*

The term "treatment" as used herein shall always refer to treating subjects for prophylactic (i.e. to prevent a disease or disorder) or therapeutic (i.e. to treat diseases or disorders regardless of their pathogenesis) purposes. Treatment of a subject will typically be therapeutic in cases of cancer disease conditions, including for example but not limited thereto breast or ovarian cancer. However, in case of patients suffering from a primary disease, which are at risk of disease progression or at risk of developing a secondary disease condition or side reaction the treatment may be prophylactic. Treatment may be effected with the pharmaceutical composition according to the invention as the sole prophylactic or therapeutic agent or else in combination with any suitable means, e.g. including chemotherapy or radiotherapy.

In oncology therapy, additional therapeutic treatments include, for instance, surgical resection, radiation therapy, chemotherapy, hormone therapy, anti-tumor vaccines, antibody-based therapies, whole body irradiation, bone marrow transplantation, peripheral blood stem cell transplantation, and the administration of chemotherapeutic agents.

Combination therapy, e.g. with respect to the combination of compounds or treatments specifically refers to the concomitant, simultaneous, parallel or consecutive treatment of a subject.

Herein provided is a pharmaceutical composition comprising the recombinant CXCL10 polypeptide or a polynucleic acid molecule or a vector as described herein, and a pharmaceutically acceptable carrier.

For treatment the pharmaceutical composition as described herein may be administered at once, or may be divided into the individual components and/or a number of smaller doses to be administered at intervals of time. The composition is typically administered at a concentration of 0.1 to 500 μg/mL, e.g. either subcutaneously, intradermal, intramuscularly, intravenous, orally, through inhalation or intra-nasally. It is understood that the precise dosage and duration of treatment is a function of the disease being treated and may be determined empirically using known testing protocols or by extrapolation from in vivo or in vitro test data.

Thus, the invention further refers to the production of the pharmaceutical composition described herein or the components thereof, and the recombinant means for such production, including an isolated nucleic acid encoding the amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press) and Sambrook et al, "Molecular Cloning: A Laboratory Manual" (4th Ed.), Vols. 1-3, Cold Spring Harbor Laboratory Press (2012).

Herein the term "subject" is understood to comprise human or mammalian subjects, including livestock animals, companion animals, and laboratory animals, in particular human beings, which are either patients suffering from a specific disease condition or healthy subjects.

Typically, such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilized carriers such as saline, Ringers solution or dextrose solution, optionally buffered with suitable buffers to a pH within a range of 5 to 8.

The formulations to be used for in vivo administration will need to be sterile. This is readily accomplished by filtration through sterile filtration membranes or other suitable methods.

Administration of the pharmaceutical composition described herein may be done in a variety of ways, including systemic or parenteral administration, preferably in the form of a sterile aqueous solution, e.g. by the intravenous, intramuscular or subcutaneous route, but also orally, intranasally, intraotically, transdermally, mucosal, topically (e.g., gels, salves, lotions, creams, etc.), intraperitoneally, intramuscularly, intrapulmonary, vaginally, parenterally, rectally or intraocularly. Thus, the invention provides for the CXCL10 mutant in a respective formulation suitable for such use.

The present invention includes treatment with a pharmaceutical preparation, containing as active substance CXCL10 mutant of the invention in a therapeutically effective amount. In particular, a pharmaceutically acceptable formulation of the CXCL10 mutant is compatible with the treatment of a subject in need thereof.

The term "therapeutically effective amount", used herein interchangeably with any of the terms "effective amount" or "sufficient amount" of the cytokine, specifically the CXCL10 of the present invention, is a quantity or activity sufficient to, when administered to the subject, effect beneficial or desired results, including clinical results, and, as such, an effective amount or synonym thereof depends upon the context in which it is being applied. In the context of disease, therapeutically effective amounts of the CXCL10 mutant are used to treat, modulate, attenuate, reverse, or affect a disease or condition that benefits from proteolytic cleavage of a target protein, for example, acute or chronic inflammatory diseases or tumor-related diseases. An effective amount is intended to mean that amount of a compound that is sufficient to treat, prevent or inhibit such diseases or disorders. The amount of the CXCL10 mutant that will correspond to such an amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

Moreover, a treatment or prevention regime of a subject with a therapeutically effective amount of the CXCL10 mutant described herein may consist of a single administration, or alternatively comprise a series of applications. For example, it may be administered at least once a day, once a week or once a month. However, in another embodiment, it may be administered to the subject multiple times a day for a given treatment. The length of the treatment period depends on a variety of factors, such as the type of disease, the severity of the disease, either acute or chronic disease, the age of the patient, the concentration and the activity of the CXCL10 mutant. It will also be appreciated that the effective dosage used for the treatment or prophylaxis may increase or decrease over the course of a particular treatment or prophylaxis regime.

The examples described herein are illustrative of the present invention and are not intended to be limitations thereon, Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

1. Materials and Methods 1.1. Molecular Structures and Modelling

All in silico studies were performed with the molecular modelling program YASARA v. 15.7.12 (www.yasara.org) (Krieger et al., 2004; Krieger and Vriend, 2014). From the CXCL10 dimeric protein structure (1O80) one of the monomers was removed and the remaining monomeric structure was energy minimized using YASARA's em_runclean macro. The macro completes missing atoms, removes bumps and corrects covalent geometry in the AMBER3 force field. It performs a steepest descent energy minimization, followed by a simulated annealing minimization in an aqueous solvent shell until energy convergence is achieved.

To assess the stability/flexibility of CXCL10, molecular dynamics simulations were performed. YASARA's "md_run" macro (www.yasara.org/md_run.mcr) cleaned the structures by adding missing hydrogens, optimized the hydrogen-bonding network, created a simulation cell, filled the cell with water and ions (0.9% NaCl), predicted pKa values, assigned protonation states according to pH 7.4, ran an initial energy minimization, assigned AMBER14 force field parameters, set initial atom velocities according to a Boltzmann distribution at 298K, started the simulation and saved snapshots every 250 picoseconds. We used the fast simulation protocol with 5 fs time-step (Krieger & Vriend, 2015). During the simulation backbone RMSD and the total energy were monitored.

1.2. Upstream- and Downstream Processing of Wild Type CXCL10 and CXCL10 Mutants

All chemicals and materials, unless stated otherwise, were obtained from Sigma-Aldrich. The protocols for the upstream- and downstream-processing of recombinant proteins were adapted from protocols of other decoy chemokines already produced in house (Falsone et al., 2013). In short: Synthetic, *E. coli* codon optimized wtCXCL10 gene cloned into pJ411 expression vectors were bought directly from ATUM. This CXCL10 gene was mutagenised using the QuikChange II PCR-aided Site-Directed Mutagenesis Kit from Agilent Technologies. For the antagonistic atgCXCL10 mutant, Asparagine on position 20 was exchanged to a lysine to increase GAG-binding affinity and the first eight amino acids, which are responsible for GPCR binding and activation, were deleted. In addition, V20 was replaced by a tryptophan residue to enable fluorescence-based interaction studies with GAGs by using isothermal fluorescence titrations (atgCXCL10*=CXCL10(Δ8,V19W,N20K)). To obtain a T-cell mobilizing CXCL10 mutant (agoCXCL10) only the N20K replacement was introduced into CXCL10. The replacement V19W exchange was only applied when fluorescence techniques were required for interaction studies (agoCXCL10*). The same was done for the wild type if fluorescence was applied (CXCL10*). PCR was performed on a Mastercycler Gradient (Eppendorf) using primers from Invitrogen and the polymerase supplied within the kit (PfuUltra High-Fidelity DNA polymerase). Plasmids were transformed into either calcium competent One Shot BL21 (DE3) *E. coli* cells when used for expression of desired protein or transformed into calcium competent One Shot Top 10 *E. coli* cells (both from Invitrogen) for plasmid amplification and storage of plasmid. To obtain plasmids from transformed cells, plasmid preparations using Quiagen Miniprep or Quiagen Midiprep Kits were performed. Correct sequences were verified by the DNA sequencing services from LGC genomics prior to expression and purification.

An upstream and downstream procedure was established adapted forwtCXCL10 and used for all mutants. For protein expression, an overnight culture of BL21 (DE3) cells, produced from a glycerol stock containing bacteria transformed with the corresponding CXCL10 plasmids, was diluted 1:1000 with LB medium (Luria-Bertani medium) containing 50 μg/mL Kanamycin sulfate. Growth conditions were: 37° C. at 220 rpm shaking. When an optical density ($OD_{600}$) of 0.8 was reached, expression was induced by adding IPTG (isopropyl β-D-thiogalactopyranosid, ThermoFisher) to a final concentration of 1 mM. After 4 additional hours of incubation, cells were harvested (6000 g, 30 min) and frozen until processed further (−80° C.). For downstream processing adequate amounts of bacterial cell pellet (usually 70 g per batch) were thawed for approximately 2 h (4° C.) and then resuspended in Lysis Buffer (50 mM Tris/HCl [Merck], 0.1% Tween-20 [Sigma], pH 8.0) using a Dounce Tissue Grinder set (Sigma). Cell suspensions were lyzed on ice using a Branson Sonifier (5×30 seconds sonification with 1 minute pause between each cycle; output control: Seven, duty cycle: constant) and then pelleted again (20 000 g, 60 min, 4° C.). These pellets (containing desired proteins aggregated into so-called inclusion bodies) were then solubilized for 60 minutes using a guanidinium chloride solution (8 M guanidinium chloride, 50 mM Tris/HCl, pH8; AlzChem). After another centrifugation step (20 000 g, 60 min, 4° C.) the supernatant was poured into cold refolding buffer (50 mM Tris/HCl [Merck], 0.1% Tween-20 [Sigma], pH 8.0) and incubated for 60 minutes. The pH of this solution was then lowered to 4.5 by dropwise addition of acetic acid (Lactan). The whole solution (usually about 2 L/batch) was then shock-diluted by slowly pouring it (1 L/min) into four-times the amount of cold deionised water. The whole amount was then subjected to (strong) cation exchange chromatography (Fractogel EMD SOs, strong cation exchanger, Merck) and a linear gradient from 50 mM Tris/HCl, pH 8.0 to 2 M NaCl, 50 mM Tris/HCl, pH 8.0 was used to elute proteins. This was followed by reversed-phase chromatography (Merck Millipore LiChrospher® RP-18) which was performed applying a non-linear gradient: from 10% acetonitrile (super gradient for HPLC; VWR International), 90% water (HPLC-grade, Merck) and 0.1% (v/v) TFA (trifluoroacetic acid) to 90% acetonitrile, 10% water, 0.1% (v/v) TFA. This HPLC step lead to a (possibly partial) unfolding of proteins, which made another cation, exchange chromatography run necessary (on-column refolding). After buffer exchange to standard PBS (10 mM $Na_xH_yPO_4$, 137 mM NaCl, pH 7.4) using Slide-A-Lyzer® dialysis cassettes (Thermo Fisher) and a concentrating step using Amicon® Centrifugal Filter Devices (MWCO: 3000 Da) protein concentration was determined and solutions where aliquoted and stored at −20° C. Purity was checked using SDS-PAGE followed by Silver-staining, according to European Molecular Biology Laboratory or Coomassie staining. Stacking gel buffer consists of 0.5M Tris-HCl with 0.4% SDS, with an pH set to 6.8 and separating gel ingredients are 1.5M Tris-HCl with 0.4% SDS with a pH of 8.8. Gels were vertically poured between 1 mm glass spacer plates and 25 mM Tris, 192 mM Glycine, 0.1% SDS, pH 8.3 was used as running buffer. The samples (proteins: 1, 2, 5 and 5 μg per slot) were mixed with sample buffer (120 mM Tris-HCl, 20% Glycerol, 4% SDS, 0.02% Bromophenol blue), heated for 5 minutes at 95° C., loaded onto the gels and electrophoresis was done for 55 minutes with constant volt set to 150. Gels were documented using GS800 Calibrated Densitometer (Biorad).

1.3. Surface Plasmon Resonance

Binding of wtCXCL10, atgCXCL10, and agoCXCL10 to heparan sulfate (Iduron; Manchester, UK) was investigated on a BiacoreX100 system (GE Healthcare, Chalfont St Giles, UK) as described earlier (Gerlza et alt, 2014). In short, measurements were performed under a steady PBS flow containing 0,005% Tween. Biotinylated HS was coupled on a pretreated C1 sensor chip and 7 different concentrations of each chemokine were measured, the second lowest concentration injected twice as control. Contact times for all injections and dissociations were 120 seconds at 30 μL/min over both Flow cells. The 1 M NaCl regeneration solution was enclosed directly after the dissociation time (300 sec) with 30 μL/min and 60 seconds contact time after each cycle. Affinity constants were assessed by a simple 1:1 equilibrium binding model, where Req is plotted against the analyte concentration. Data was fitted using the steady state formula that corresponds to the Langmuir adsorption equation, provided by the Biacore Evaluation Software.

1.4. Isothermal Fluorescence Titration

Titration experiments with Heparan Sulfate (Iduron) were performed on a Fluoromax-4 Spectrofluorometer (Horiba; Kyoto). 700 nM of V19W CXCL10 mutant solutions were equilibrated for 30 minutes before measurement and spectra were recorded upon excitation at 280 nm over the range of 300-400 nm. Aliquots of HS ligand in concentrations ranging from 50 nM to 500 nM were added and after an equilibration period of 1 minute, spectra were recorded. For background correction, the same HS concentrations were added to PBS as described for protein solutions and spectra were subtracted from protein samples. The use of a very concentrated GAG oligosaccharide stock solution ensured a dilution of the protein sample less than 5%. The slit widths were set at 5 nm for excitation and emission. Scan speed was set at 500 nm/min and the temperature set to 20° C. After background subtraction, the fluorescence intensity, F, was integrated, and the mean values resulting from 3 independent measurements were plotted against the concentration of the added ligand. The resulting binding isotherms were analysed by nonlinear regression using the program Origin (Microcal Inc., Northampton) as described before.

1.5. Chemotaxis Assay 1.5.1. Cells and Stimulation of Cells

Primary PBMCs (peripheral blood mononuclear cells) were isolated from whole blood collected from healthy, male, Caucasian volunteers. Isolation was carried out using a Ficoll Paque density gradient (GE Healthcare). The collected so-called buffy coat (containing lymphocytes like T cells, B cells and NK cells as well as monocytes) was washed using HBSS−/− (Hanks' Balanced Salt solution without calcium and with magnesium, Gibco) and then transferred into appropriate medium and incubated: RPMI medium (Sigma) containing 10% FCS (fetal calf serum), 2 mM L-glutamine, 100 units/ml penicillin, and 100 U/ml streptomycin at 37° C. and 5% (v/v) $CO_2$. To activate PBMCs the cells were treated with PHA-L (phytohemagglutinin, 2 μg/mL, Sigma) and with IL-2 (interleukin-2, 50 U/mL, Sigma) for additional 12 days. Media (containing fresh IL-2) was exchanged every third day. Immediately before performing the assay, cells were washed and resuspended using HBSS+/+(Hanks' Balanced Salt solution with calcium and with magnesium, Gibco) to a final concentration of $2\times10^6$ cells/ml (calculated to the quota of T-cells).

1.5.2. Boyden Chamber Assay

The ability of the CXCL10 variants to induce migration of T-lymphocytes was tested using a 48-well Boyden chamber system (Neuroprobe) with a polycarbonate, PVP− (polyvinylpyrrolidone−) free cell culture membrane (25×80 mm, 5 μm pore size, GE Healthcare). Dilution series of chemokines and mutants ranging from 750 nM to 250 nM in PBS were placed in the lower wells of the chamber, 50 μL of cell suspension ($2\times10^6$ cells per ml) per well was added in the upper part of the chamber. After 2 h of migration period at 37° C. and 5% C02 (v/v), the membrane was removed, washed with HBSS−/− and air-dried. The migrated cells were fixed with MeOH and stained with red and blue Hemacolor stain (Merck). The chemotactic index (total amount of migrated cells per randomly migrated cells) was determined using the 40 times magnification of a microscope (five photos per well were taken; per dilution the average of 12 wells, was calculated). The chemotactic index (CI) was calculated as follows: total number of cells migrated towards a certain chemokine concentration per number of randomly migrated cells towards buffer.

1.6. Transmigratory Assay

Transmigratory assay was performed using HTS Transwell plates (96 well plate, polycarbonate membrane with 5 μm pore size, Corning, New York, NY, USA). Before seeding of cells, the plates were coated with 1.6 μg Collagen in 40 μL 0.1% acetic acid per well in the upper compartment. After 2 hours of incubation at 37 C the wells were washed once with HBSS−/− and plates were air dried, incubated for 2 hours at 37° C. 35 000 human EA.hy926 (ATCC, Manassas, VA, USA) endothelial cells were seeded in the upper compartment in full growth medium (DMEM, 10% FBS, 4 mmol/L L-Glutamine and 1% Penicillin/Streptomycin 1:100, Gibco). After 48 hours of endothelial cell growth, the cells were stimulated with 50 ng/mL human TNF-α on the day of the assay. T-cells, which were stimulated as described for Boyden chamber assay, were harvested, labelled with 2 μmol/L calcein acetoxymethyl ester (AM, Sigma 17783) for 30 minutes at 37° C. and 200 000 cells, followed by 2 times washing with HBSS−/− and final resuspension in HBSS+/+ (Gibco) with 20 mmol/L HEPES (Sigma) to a final concentration of $2.10^5$ cells/40 μL (in each well).

Different concentrations of CXCL10 variants were pipetted into the lower compartment and migration took place for 2 hours at 37 C and 5% C02. Fluorescence intensity of the migrated cells was recorded using SpectraMax M3 Plate reader (Molecular Devices, San Jose, CA, USA) and Data were analysed using GraphPad software.

1.7. Statistical Analysis

For the SPR, Boyden chamber and transmigratory assays, all data are shown as mean+SEM for n observations. All experiments were repeated three times and statistical analyses was performed by GraphPad v5.04 using Student's t-test. *P<0.05, P<0.01 and *P<0.001 were considered as statistically significant.

2. Results and Discussion 2.1. Structural Analysis and MD Simulations

The three-dimensional structure of CXCL10 is well documented (1O80.pdb), likewise well-known is the GAG-binding site of the chemokine. Here a rigorous structural analysis of the chemokine was performed following a 0.5 ns molecular dynamic simulation. By this means the regions in the GAG-binding site should be identified which are flexible enough to accommodate an additional lysine residue and which sticks out from the GAG interaction interface which would therefore enable the modified amino acid to engage in GAG binding. According to a rigorous structural analysis, the N-terminal loop was recognized to be the most promising site for potential mutagenesis. Various site-directed replacement mutants (exchange to K) have been generated to increase the GAG-binding affinity by addressing the amino acids 112, 114, N20, and E25 individually as well as in combinations thereof (data not shown). By this means, the N20K individual replacement mutant was found to be superior compared to the other mutants. By "superior" meant herein is the balance of increased affinity in relation to the number of amino acid changes required to improve GAG-binding affinity, i.e. adding further replacements to N20K did not increase significantly the affinity towards GAGs.

2.2. Determination of GAG-Binding Affinity

Two methods were applied to investigate GAG-binding affinity of the CXCL10 variants. Surface plasmon resonance (SPR) was used to study the effect of CXCL10 mutants binding to heparan sulfate immobilized via a biotin tag onto a neutravidin-coated Biacore chip. This method is indicative for interaction events sensed by the GAG molecule (which is the receptor in this case). In addition, isothermal fluorescence titrations (IFTs) were applied to quantitate ligand binding by sensing of the chemokine variants (which were the receptors in this case). For this purpose, an additional mutation had to be introduced into CXCL10, namely V19W, since there is no conformationally sensitive fluorophore—a tryptophan residue—contained in the sequence of CXCL10. Comparing SPR and IFT should enable interpretation of the increase in GAG-binding affinity with respect to binding sites on both molecules.

FIG. 1 shows binding isotherms of wtCXCL10 and agoCXCL10 binding to HS as determined by surface plasmon resonance. In the insert the respective Kd values are shown.

The difference in HS binding affinity of wtCXCL10 and agoCXCL10 was first investigated: the single N20K mutation induced a 20-fold increase in the chemokine's affinity for its GAG ligand (see FIG. 1). Interestingly, by comparing wtCXCL10* and agoCXCL10* in IFT measurements a significant difference in HS binding affinity was also observed (see FIG. 2). As indicated above, this different observation from two methods could be related to more binding sites on the ("receptor") GAG for the CXCL10 proteins as recorded by SPR, compared to less binding sites for HS on the ("receptor") chemokine as detected by IFT. In the data fitting models used here, the well-known molecular concentrations of proteins and glycans are considered and not the concentration of binding sites on both interaction partners, which are not known. This is further complicated by the fact that binding of chemokines to GAGs leads often to an oligomerization of the proteins which further changes the number of accessible binding sites for GAGs per mole chemokine. In the following we therefore focused on IFT affinity measurements since it may be assumed that the number of GAG binding sites per chemokine monomer remains constant at one.

Adding a delta8 N-terminal deletion to the N20K replacement mutation, which aimed at an antagonistic CXCL10 mutant, lead to a slight further increase in HS binding affinity as detected by IFT (see FIG. 2; in independent SPR measurements it was shown that the V19W mutation did not affect the GAG binding affinity of CXCL10; data not shown). This small, potentially non-significant, increase in affinity could be interpreted by the missing flexible N-terminus in atgCXCL10* which is entropically favorable compared to the intact N-Terminus in agoCXCL10*.

FIG. 2 shows binding isotherms of wtCXCL10*, agoCXCL10* and atgCXCL10* binding to HS as determined by isothermal fluorescence titration. In the insert the respective Kd values are shown.

2.3. Chemotaxis Assay

Using mononuclear cells isolated from fresh whole blood from healthy, male Caucasians the ability of different concentrations of wtCXCL10 and mutants thereof to induce migration of lymphocytes (PHA-L/1 L2 stimulated T-cells) was investigated in a 48-well Boyden Chamber set-up. Even though this assay clearly lacks many components of in vivo migration—such as (haptotactic) chemokine gradient, chemokine presentation by endothelial cells, and physiologic flow—it was interesting to compare wtCXCL10-induced migration with potential T-cell mobilisation induced by atgCXCL10 and agoCXCL10, especially with respect to the mutual influence of GAGs on GPC receptor activation.

As displayed in FIG. 3, wtCXCL10 exhibited the typical inverse dose-dependence of chemokine-induced chemotaxis (relating to GPC receptor internalization at high chemokine concentrations), whereas atgCXCL10 was unable to induce T-cell migration at any of the indicated concentrations. On the other hand, agoCXCL10 displayed significantly improved T-cell chemotaxis at the two lower concentrations applied in the assay. This result was quite unexpected since it has been generally assumed that the influence of GAG co-receptors on immune cell migration is exerted (in trans) by GAGs located on the target tissue endothelium and not by GAGs on the immune cells (in cis).

FIG. 3 shows the chemotactic activity of CXCL10, agoCXCL10 and atgCXCL10 on stimulated T-cells using Boyden chamber assay. The chemotactic index (CI) represents the mean cell number of migrated cells divided through the mean cell number of background migration. *$p<0.05$, $p<0.01$, *$p<0.001$ was considered as statistically significant.

2.4. Transmigration Assay

Also, the influence of endothelial GAGs was considered by quantifying the chemotactic potency of our CXCL10 variants in a typical transmigration assay (see FIG. 4). In this set-up, wtCXCL10 exhibited a direct dose-response, and in which atgCXCL10 was expectedly unable to induce T-cell migration. Like in the Boyden chamber, agoCXCL10 showed a significantly increased T-cell mobilization in the transwell set-up, but unlike in the Boyden chamber chemotaxis was improved at all three chemokine concentrations tested. Engineering increased GAG-binding affinity into CXCL10 apparently leads to improved T-cell mobilization. This could open up new ways to treat severe diseases in which the natural T-cell response is suppressed like in many solid tumors. In addition, our results can be interpreted that CXCL10-induced chemotaxis is dependent on GAGs located on both endothelial and T-cells. In future studies we will explore the direct interaction of GAGs, CXCL10 and CXCR3 in a triple complex on T-calls.

FIG. 4 shows in vitro transendothelial migration of T-cells upon stimulation with CXCL10, agoCXCL1G and atgCXCL10 on stimulated T-cells using Boyden chamber assay. The migration was background corrected and data sets were compared to their respective wild-type concentration using Ttest. *$p<0.05$, $p<0.01$ *$p<0.001$ was considered as statistically significant.

3. Concluding Remarks

Chemokines are important mediators of various immunological diseases, amongst them oncological disorders. On top of the typical and well-studied GPC receptors on immune cells, it has become evident over recent years that chemokine activity is dependent also on glycosaminoglycans (GAGs), which are located on all human cells as well as in the extracellular matrix. In previous engineering studies inventors were able to generate chemokine mutants which inhibit immune cell migration (Adage et al., 2012). Here it is surprisingly shown for the first time that by increasing the affinity for GAGs on immune cells, the chemotactic activity of the chemokine CXCL10 for its target T-cells could be significantly increased. This approach can be used to generate a novel class of immune cell mobilizing biologics for different indications.

Example 2

FIG. 6 shows the experimental outline of tumor progression in the 4T1 murine breast cancer model (Pulaski & Ostrand-Rosenberg, 2001), as well as the treatment scheme with the HSA-CXCL10 N20K (ATG-H06) construct. This protein is the agoCXCL10 mutant fused C-terminally to human serum albumin (HSA, see also amino acid sequence in FIG. 5). Tumor formation/growth was induced by inguinal injection of 4T1 mammary carcinoma cells. The compound was applied i.v. at day 22 and again i.p. at day 24.

After 30 days the animals were sacrificed, the tumors removed and analysed with respect to cell infiltration.

FIG. 7 displays the results of the 4T1 murine breast cancer model: in the top panel, the increase in weight of the solid tumors following treatment with HSA-CXCL10 N20K (ATG-H06) is shown. In the lower panel, the FACS analysis of the murine lungs with respect to T-cell infiltration is displayed.

REFERENCES

Adage T, Piccinini A M, Falsone A, Trinker M, Robinson J, Gesslbauer B, Kungi A J. (2012) Structure-based design of decoy chemokines as a way to explore the pharmacological potential of glycosaminoglycans. *Br J Pharmacol.* 167, 1195-1205.

Bernfield M., Götte M., Park P. W., Reizes O., Fitzgerald M. L., Lincecum J. and Zako M. (1999) Functions of cell surface heparan sulfate proteoglycans. *Annual review of biochemistry,* 68, 729-777.

Booth V., Keizer D. W., Kamphuis M. B., Clark-Lewis I. and Sykes B. D. (2002) The CXCR3 binding chemokine IP-10/CXCL10: structure and receptor interactions. *Biochemistry,* 41, 10418-10425.

Campanella G. S., Grimm J., Manice L. A., Colvin R. A., Medoff B. D., Wojtkiewicz G. R., Weissleder R. and Luster A. D. (2006) Oligomerization of CXCL10 is necessary for endothelial cell presentation and in vivo activity. *The Journal of Immunology,* 177, 6991-6998.

Campanella G. S., Lee E. M., Sun J. and Luster A. D. (2003) CXCR3 and heparin binding sites of the chemokine IP-10 (CXCL10). *Journal of biological chemistry.*

Fadnes B., HusebekkA., Svineng G., Rekdal Ø., Yanagishita M., Kolset S. O. and Uhlin-Hansen L. (2012) The proteoglycan repertoire of lymphoid cells. *Glycoconjugate journal,* 29, 513-523.

Falsone A., Wabitsch V., Geretti E., Potzinger H., Geriza T., Robinson J., Adage T., Teixeira M. M. and Kungl A. J. (2013) Designing CXCL8-based decoy proteins with strong anti-inflammatory activity in vivo. *Bioscience reports,* 33, 743-754.

Falsone A., Wabitsch V., Geretti E., Potzinger H., Geriza T., Robinson J., Adage T., Teixeira M. M. and Kungl A. J. (2013) Designing CXCL8-based decoy proteins with strong anti-inflammatory activity in vivo. *Biosci Rep,* 33.

Gattass C. R., King L. B., Luster A. D. and Ashwell J. D. (1994) Constitutive expression of interferon gamma-inducible protein 10 in lymphoid organs and inducible expression in T cells and thymocytes. *Journal of Experimental Medicine,* 179, 1373-1378.

Gerlza T., Hecher B., Jeremic D., Fuchs T., Gschwandtner M., Falsone A., Gesslbauer B. and Kungl A. J. (2014) A Combinatorial Approach to Biophysically Characterise Chemokine-Clycan Binding Affinities for Drug Development. *Molecules,* 19, 10618-10634.

Handel T. M., Johnson Z., Crown S. E., Lau E. K., Sweeney M. and Proudfoot A. E. (2005) Regulation of Protein Function by Glycosaminoglycans—as exemplified by Chemokines. *Annual review of biochemistry,* 74, 385-410.

Hileman R. E., Fromm J. R., Weiler J L M. and Linhardt R. J. (1993) Glycosaminoglycan-protein interactions: definition of consensus sites in glycosaminoglycan binding proteins. *Bioessays,* 20, 156-167.

Hoogewerf A. J., Kuschert G. S., Proudfoot A. E., Borlat F., Clark-Lewis I., Power C. A. and Wells T. N. (1997) Glycosaminoglycans mediate cell surface oligomerization of chemokines. *Biochemistry,* 36, 13570-13578.

Jabeen T., Leonard P., Jamaluddin H. and Acharya K. R. (2003) *Structure of mouse IP-*10, *a chemokine. Acta Crystallographica Section D: Biological Crystallography,* 64, 611-619.

Jiang D., Liang J., Campanella G. S., Guo R., Yu S., Xie T., Liu N., Jung Y., Homer R. and Meltzer E. B. (2010) Inhibition of pulmonary fibrosis in mice by CXCL10 requires glycosaminoglycan binding and syndecan-4. *The Journal of clinical investigation,* 120, 2049-2057.

Khan I. A., MacLean J. A., Lee F. S., Casciotti L., DeHaan E., Schwartzman J. D. and Luster A. D. (2000) IP-10 is critical for effector T cell trafficking and host survival in Toxoplasma gondii infection. *Immunity,* 12, 483-494.

Lindahl U. and Kjellén L. (2013) Pathophysiology of heparan sulphate: many diseases, few drugs. *Journal of internal medicine,* 273, 555-571.

Luster A. D., Greenberg S. M. and Leder P. (1995) The IP-10 chemokine binds to a specific cell surface heparan sulfate site shared with platelet factor 4 and inhibits endothelial cell proliferation. *The Journal of experimental medicine,* 182, 219-231.

Luster A. D., Greenberg S. M. and Leder P. (1995) The IP-10 chemokine binds to a specific cell surface heparan sulfate site shared with platelet factor 4 and inhibits endothelial cell proliferation. *J Exp Med,* 182, 219-231.

Mach F., Sauty A., Iarossi A. S., Sukhova G. K., Neote K., Libby P. and Luster A. D. (1999) Differential expression of three T lymphocyte-activating CXC chemokines by human atheroma-associated cells. *The Journal of clinical investigation,* 104, 1041-1050

Medoff B. D., Sauty A., Tager A. M., Maclean J. A., Smith R. N., Mathew A., Dufour J. H. and Luster A. D. (2002) IFN-γ-inducible protein 10 (CXCL10) contributes to airway hyperreactivity and airway inflammation in a mouse model of asthma. *The Journal of immunology,* 168, 5278-5286.

Moelants E. A., Van Damme J. and Proost P. (2011) Detection and quantification of citrullinated chemokines. *PLoS One,* 6, e28976.

Moser B. and Willimann K. (2004) Chemokines: role in inflammation and immune surveillance. *Annals of the rheumatic diseases,* 63, ii84-ii89.

Murdoch C. and Finn A. (2000) Chemokine receptors and their role in inflammation and infectious diseases. *Blood,* 95, 3032-3043.

Neel N. F., Schutyser E., Sai J., Fan G.-H. and Richmond A. (2005) Chemokine receptor internalization and intracellular trafficking. *Cytokine & growth factor reviews,* 16, 637-658.

Parish C. R. (2006) The role of heparan sulphate in inflammation. *Nature Reviews immunology,* 6, 633-643.

Pignatti P., Brunetti G., Moretto D., Yacoub M.-R., Fiori M., Balbi B., Balestrino A., Cervio G., Nava S. and Moscato G. (2006) Role of the chemokine receptors CXCR3 and CCR4 in human pulmonary fibrosis. *American journal of respiratory and critical care medicine,* 173, 310-317.

Proost P., Wuyts A. and Van Damme J. (1996) The role of chemokines in inflammation. *International Journal of Clinical and Laboratory Research,* 26, 211-223. Pulaski, B A. and Ostrand-Rosenberg, S. (2001) Mouse 4T1 breast tumor model. *Curr Protoc Immunol.*; Chapter 20:Unit 20.2

Saetta M., Mariani M., Panina-Bordignon P., Turato G., Buonsanti C., Baraldo S., Bellettato C. M., Papi A., Corbetta L. and Zuin R. (2002) Increased expression of the chemokine receptor CXCR3 and its ligand CXCL10 in peripheral airways of smokers with chronic obstructive pulmonary disease. *American journal of respiratory and critical care medicine,* 165, 1404-1409.

Salanga C. and Handel T. (2011) Chemokine oligomerization and interactions with receptors and glycosaminoglycans: the role of structural dynamics in function. *Experimental cell research,* 317, 590-601.

Shimada A., Oikawa Y., Yamada Y., Okubo Y. and Narumi S. (2009) The role of the CXCL10/CXCR3 system in type 1 diabetes. The review of diabetic studies: RDS, 6, 81.

Sørensen T. L., Tani M., Jensen J., Pierce V., Lucchinetti C., Folcik V. A., Qin S., Rottman J., Sellebjerg F. and Strieter R. M. (1999) Expression of specific chemokines and chemokine receptors in the central nervous system of multiple sclerosis patients. *The Journal of clinical investigation,* 103, 807-815.

Swaminathan G. J., Holloway D. E., Colvin R. A., Campanella G. K., Papageorgiou A. C., Luster A. D. and Acharya K. R. (2003) Crystal structures of oligomeric forms of the IP-10/CXCL10 chemokine. *Structure,* 11, 521-532.

Tager A. M., Kradin R. L., LaCamera P., Bercury S. D., Campanella G. S., Leary C. P., Polosukhin V., Zhao L.-H., Sakarnoto H. and Blackwell T. S. (2004) Inhibition of pulmonary fibrosis by the chemokine IP-10/CXCL10. *American ournal of respiratory cell and molecular biology,* 31, 395-404.

Trinker M. U. and Kungl A. J. (2013) Targeting chemokine-glycan interactions: the CellJammer® technology platform. *Drug Discovery Today: Technologies,* 9, e253-e259.

Vives R. R., Sadir R., Imberty A., Rencurosi A. and Lortat-Jacob H. (2002) A kinetics and modeling study of RANTES (9-68) binding to heparin reveals a mechanism of cooperative oligomerization. *Biochemistry,* 41, 14779-14789.

Webb L. M., Ehrengruber M. U., Clark-Lewis I., Baggiolini M. and Rot A. (1993) Binding to heparan sulfate or heparin enhances neutrophil responses to interleukin 8. *Proceedings of the National Academy of Sciences,* 90, 7158-7162.

Weng Y., Siciliano S. J, Waldburger K. E., Sirotina-Meisher A., Staruch M. J., Daugherty B. L., Gould S. L., Springer M. S. and Demartino J. A. (1998) Binding and functional properties of recombinant and endogenous CXCR3 chemokine receptors. *Journal of biological chemistry,* 273, 18288-18291.

Yang J. and Richmond A. (2004) The angiostatic activity of interferon-inducible protein-10/CXCL10 in human melanoma depends on binding to CXCR3 but not to glycosaminoglycan. *Molecular Therapy* 9, 846-855.

The invention claimed is:

1. A recombinant CXCL10 polypeptide with increased glycosaminoglycan (GAG) binding affinity compared to wild type CXCL10, comprising an amino acid sequence having at least 95% sequence identity with SEQ ID NO: 1, wherein the amino acid sequence at position 20 of SEQ ID NO: 1 is substituted with lysine, and optionally wherein the amino acid sequence at positions 12, 14, or 25 of SEQ ID NO: 1 is further substituted with lysine.

2. The recombinant CXCL10 polypeptide according to claim 1, wherein the amino acid sequence has at least 96%, 97%, 98%, or 99% sequence identity with SEQ ID NO: 1 and comprises a Lysine at position 20 of SEQ ID NO: 1.

3. The recombinant CXCL10 polypeptide according to claim 1, comprising the amino acid sequence of the formula:

VPLSRTVRCTC(X1)S(X2)SNQPV(X3)PRSL(X4) KLEIIPASQFCPRVEIIATMKKKG EKR-CLNPESKAIKNLLKAVSKERSKRSP (SEQ ID NO: 3),

X1,

X2,

X3, and

X4 are K.

4. The recombinant CXCL10 polypeptide according to claim 1, wherein amino acids at positions 1, 1-2, 1-3, 1-4, 1-5, 1-6, 1-7, or 1-8 of SEQ ID NO: 1 are deleted.

5. The recombinant CXCL10 polypeptide according to claim 1, wherein the polypeptide comprises the sequence of any one of SEQ ID NO: 2, SEQ ID NO: 7, SEQ ID NO: 10, or SEQ ID NO: 11.

6. The recombinant CXCL10 polypeptide according to claim 1, wherein said CXCL10 polypeptide has at least 2-fold, at least 5-fold, or at least 10-fold increased affinity for GAG compared to wild type CXCL10 of SEQ ID NO: 1.

7. The recombinant CXCL10 polypeptide according to claim 1, wherein said CXCL10 polypeptide comprises one or more tag sequences.

8. The recombinant CXCL10 polypeptide according to claim 7, comprising one or more linker sequences inserted between the CXCL10 polypeptide and the tag sequence.

9. The recombinant CXCL10 polypeptide according to claim 1, wherein the polypeptide comprises the sequence of SEQ ID NO: 12.

10. An isolated polynucleic acid molecule encoding the recombinant CXCL10 polypeptide according claim 1.

11. The isolated polynucleic acid molecule according to claim 10, wherein the molecule is incorporated into a vector.

12. The isolated polynucleic acid molecule according to claim 11, wherein the vector is transfected into a recombinant non-human cell.

13. A pharmaceutical composition comprising the recombinant CXCL10 polypeptide according to claim 1 and a pharmaceutically acceptable carrier.

14. A method of treating a solid tumor in a subject comprising administering an effective amount of the recombinant CXCL10 polypeptide according to claim 1 to the subject.

15. The recombinant CXCL10 polypeptide according to claim 7, wherein the tag sequences are tag sequences of human serum albumin or Fc parts of antibodies.

16. The recombinant CXCL10 polypeptide according to claim 8, wherein the linker sequence is GGGS.

* * * * *

SEQUENCE LISTING

```
<160> NUMBER OF SEQ ID NOS: 20

<210> SEQ ID NO 1
<211> LENGTH: 77
<212> TYPE: PRT
<213> ORGANISM: Homo sapiens

<400> SEQUENCE: 1

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75


<210> SEQ ID NO 2
<211> LENGTH: 77
<212> TYPE: PRT
<213> ORGANISM: Artificial Sequence
<220> FEATURE:
<223> OTHER INFORMATION: CXCL10

<400> SEQUENCE: 2

Val Pro Leu Ser Arg Thr Val Arg Cys Thr Cys Ile Ser Ile Ser Asn
1               5                   10                  15

Gln Pro Val Lys Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60
```

Leu Lys Ala Val Ser Lys Glu Arg Ser Lys Arg Ser Pro
65 70 75

<210> SEQ ID NO 3
<211> LENGTH: 77
<212> TYPE: PRT
<213> ORGANISM: Artificial Sequence
<220> FEATURE:
<223> OTHER INFORMATION: CXCL10
<220> FEATURE:
<221> NAME/KEY: MISC_FEATURE
<222> LOCATION: (12)..(12)
<223> OTHER INFORMATION: X is I, K or R
<220> FEATURE:
<221> NAME/KEY: MISC_FEATURE
<222> LOCATION: (14)..(14)
<223> OTHER INFORMATION: X is I, K or R
<220> FEATURE:
<221> NAME/KEY: MISC_FEATURE
<222> LOCATION: (20)..(20)
<223> OTHER INFORMATION: X is N, K or R
<220> FEATURE:
<221> NAME/KEY: MISC_FEATURE
<222> LOCATION: (25)..(25)
<223> OTHER INFORMATION: X is E, K or R

<400> SEQUENCE: 3

Val Pro Leu Ser Arg Thr Val Arg Cys Thr Cys Xaa Ser Xaa Ser Asn
1 5 10 15

Gln Pro Val Xaa Pro Arg Ser Leu Xaa Lys Leu Glu Ile Ile Pro Ala
20 25 30

Ser Gln Phe Cys Pro Arg Val Glu Ile Ile Ala Thr Met Lys Lys Lys
35 40 45

Gly Glu Lys Arg Cys Leu Asn Pro Glu Ser Lys Ala Ile Lys Asn Leu
50 55 60

Leu Lys Ala Val Ser Lys Glu Arg Ser Lys Arg Ser Pro
65 70 75

<210> SEQ ID NO 4
<211> LENGTH: 237
<212> TYPE: DNA
<213> ORGANISM: Homo sapiens

<400> SEQUENCE: 4
atggtcccgt tgtcccgcac tgtccgctgt acttgtattt cgatttctaa ccaaccagtc 60
aatccgcgta gcctggagaa gctggaaatc atcccggcca gccagttctg cccgcgtgtg 120
gagatcattg cgaccatgaa gaagaaaggt gagaaacgtt gcctgaaccc ggaaagcaaa 180
gcgatcaaaa atctgctgaa ggcagttagc aaagaacgta gcaagcgcag cccgtaa 237

<210> SEQ ID NO 5
<211> LENGTH: 237
<212> TYPE: DNA
<213> ORGANISM: Artificial Sequence
<220> FEATURE:
<223> OTHER INFORMATION: CXCL10

<400> SEQUENCE: 5
atggtcccgc tgtcccgtac cgttcgctgc acttgtattt ctattagcaa ccagccggtc 60
aagccgcgct cgctggaaaa actggagatc atcccggcaa gccaattctg tccgcgtgtt 120
gaaatcattg ccacgatgaa gaagaaaggt gagaagcgtt gcctgaaccc agaaagcaaa 180
gcgatcaaaa atctgttgaa ggcggtgagc aaagagcgca gcaagcgtag cccgtaa 237

<210> SEQ ID NO 6
<211> LENGTH: 62
<212> TYPE: PRT
<213> ORGANISM: Artificial Sequence
<220> FEATURE:
<223> OTHER INFORMATION: CXCL10

<400> SEQUENCE: 6

```
Cys Thr Cys Ile Ser Ile Ser Asn Gln Pro Val Asn Pro Arg Ser Leu
1               5                   10                  15

Lys Lys Leu Glu Ile Ile Pro Ala Ser Gln Phe Cys Pro Arg Val Glu
            20                  25                  30

Ile Ile Ala Thr Met Lys Lys Lys Gly Glu Lys Arg Cys Leu Asn Pro
        35                  40                  45

Glu Ser Lys Ala Ile Lys Asn Leu Leu Lys Ala Val Ser Lys
    50                  55                  60
```

<210> SEQ ID NO 7
<211> LENGTH: 69
<212> TYPE: PRT
<213> ORGANISM: Artificial Sequence
<220> FEATURE:
<223> OTHER INFORMATION: CXCL10

<400> SEQUENCE: 7

```
Cys Thr Cys Ile Ser Ile Ser Asn Gln Pro Val Lys Pro Arg Ser Leu
1               5                   10                  15

Glu Lys Leu Glu Ile Ile Pro Ala Ser Gln Phe Cys Pro Arg Val Glu
            20                  25                  30

Ile Ile Ala Thr Met Lys Lys Lys Gly Glu Lys Arg Cys Leu Asn Pro
        35                  40                  45

Glu Ser Lys Ala Ile Lys Asn Leu Leu Lys Ala Val Ser Lys Glu Arg
    50                  55                  60

Ser Lys Arg Ser Pro
65
```

<210> SEQ ID NO 8
<211> LENGTH: 69
<212> TYPE: PRT
<213> ORGANISM: Artificial Sequence
<220> FEATURE:
<223> OTHER INFORMATION: CXCL10

<400> SEQUENCE: 8

```
Cys Thr Cys Lys Ser Ile Ser Asn Gln Pro Val Asn Pro Arg Ser Leu
1               5                   10                  15

Glu Lys Leu Glu Ile Ile Pro Ala Ser Gln Phe Cys Pro Arg Val Glu
            20                  25                  30

Ile Ile Ala Thr Met Lys Lys Lys Gly Glu Lys Arg Cys Leu Asn Pro
        35                  40                  45

Glu Ser Lys Ala Ile Lys Asn Leu Leu Lys Ala Val Ser Lys Glu Arg
    50                  55                  60

Ser Lys Arg Ser Pro
65
```

<210> SEQ ID NO 9
<211> LENGTH: 69
<212> TYPE: PRT
<213> ORGANISM: Artificial Sequence
<220> FEATURE:
<223> OTHER INFORMATION: CXCL10

<400> SEQUENCE: 9

Cys Thr Cys Lys Ser Ile Ser Asn Gln Pro Val Asn Pro Arg Ser Leu
1 5 10 15

Lys Lys Leu Glu Ile Ile Pro Ala Ser Gln Phe Cys Pro Arg Val Glu
20 25 30

Ile Ile Ala Thr Met Lys Lys Lys Gly Glu Lys Arg Cys Leu Asn Pro
35 40 45

Glu Ser Lys Ala Ile Lys Asn Leu Leu Lys Ala Val Ser Lys Glu Arg
50 55 60

Ser Lys Arg Ser Pro
65

<210> SEQ ID NO 10
<211> LENGTH: 69
<212> TYPE: PRT
<213> ORGANISM: Artificial Sequence
<220> FEATURE:
<223> OTHER INFORMATION: CXCL10

<400> SEQUENCE: 10

Cys Thr Cys Lys Ser Ile Ser Asn Gln Pro Val Lys Pro Arg Ser Leu
1 5 10 15

Lys Lys Leu Glu Ile Ile Pro Ala Ser Gln Phe Cys Pro Arg Val Glu
20 25 30

Ile Ile Ala Thr Met Lys Lys Lys Gly Glu Lys Arg Cys Leu Asn Pro
35 40 45

Glu Ser Lys Ala Ile Lys Asn Leu Leu Lys Ala Val Ser Lys Glu Arg
50 55 60

Ser Lys Arg Ser Pro
65

<210> SEQ ID NO 11
<211> LENGTH: 69
<212> TYPE: PRT
<213> ORGANISM: Artificial Sequence
<220> FEATURE:
<223> OTHER INFORMATION: CXCL10

<400> SEQUENCE: 11

Cys Thr Cys Lys Ser Lys Ser Asn Gln Pro Val Lys Pro Arg Ser Leu
1 5 10 15

Lys Lys Leu Glu Ile Ile Pro Ala Ser Gln Phe Cys Pro Arg Val Glu
20 25 30

Ile Ile Ala Thr Met Lys Lys Lys Gly Glu Lys Arg Cys Leu Asn Pro
35 40 45

Glu Ser Lys Ala Ile Lys Asn Leu Leu Lys Ala Val Ser Lys Glu Arg
50 55 60

Ser Lys Arg Ser Pro
65

<210> SEQ ID NO 12
<211> LENGTH: 675
<212> TYPE: PRT
<213> ORGANISM: Artificial Sequence
<220> FEATURE:
<223> OTHER INFORMATION: CXCL10

<400> SEQUENCE: 12

Val Pro Leu Ser Arg Thr Val Arg Asp Ala His Lys Ser Glu Val Ala
1 5 10 15

```
His Arg Phe Lys Asp Leu Gly Glu Glu Asn Phe Lys Ala Leu Val Leu
            20                  25                  30

Ile Ala Phe Ala Gln Tyr Leu Gln Gln Ala Pro Phe Glu Asp His Val
        35                  40                  45

Lys Leu Val Asn Glu Val Thr Glu Phe Ala Lys Thr Cys Val Ala Asp
    50                  55                  60

Glu Ser Ala Glu Asn Cys Asp Lys Ser Leu His Thr Leu Phe Gly Asp
65                  70                  75                  80

Lys Leu Cys Thr Val Ala Thr Leu Arg Glu Thr Tyr Gly Glu Met Ala
                85                  90                  95

Asp Cys Cys Ala Lys Gln Glu Pro Glu Arg Asn Glu Cys Phe Leu Gln
            100                 105                 110

His Lys Asp Asp Asn Pro Asn Leu Pro Arg Leu Val Arg Pro Glu Val
        115                 120                 125

Asp Val Met Cys Thr Ala Phe His Asp Asn Glu Glu Thr Phe Leu Lys
    130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
    210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
        275                 280                 285

Lys Pro Leu Leu Glu Lys Ser His Cys Ile Ala Glu Val Glu Asn Asp
    290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350

Leu Leu Leu Arg Leu Ala Lys Thr Tyr Glu Thr Thr Leu Glu Lys Cys
        355                 360                 365

Cys Ala Ala Ala Asp Pro His Glu Cys Tyr Ala Lys Val Phe Asp Glu
    370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430
```

```
Glu Val Ser Arg Asn Leu Gly Lys Val Gly Ser Lys Cys Cys Lys His
        435                 440                 445

Pro Glu Ala Lys Arg Met Pro Cys Ala Glu Asp Tyr Leu Ser Val Val
    450                 455                 460

Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
            500                 505                 510

Glu Thr Phe Thr Phe His Ala Asp Ile Cys Thr Leu Ser Glu Lys Glu
        515                 520                 525

Arg Gln Ile Lys Lys Gln Thr Ala Leu Val Glu Leu Val Lys His Lys
    530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
            580                 585                 590

Leu Gly Gly Gly Gly Ser Val Pro Leu Ser Arg Thr Val Arg Cys Thr
        595                 600                 605

Cys Ile Ser Ile Ser Asn Gln Pro Val Lys Pro Arg Ser Leu Glu Lys
    610                 615                 620

Leu Glu Ile Ile Pro Ala Ser Gln Phe Cys Pro Arg Val Glu Ile Ile
625                 630                 635                 640

Ala Thr Met Lys Lys Lys Gly Glu Lys Arg Cys Leu Asn Pro Glu Ser
                645                 650                 655

Lys Ala Ile Lys Asn Leu Leu Lys Ala Val Ser Lys Glu Arg Ser Lys
            660                 665                 670

Arg Ser Pro
        675


<210> SEQ ID NO 13
<211> LENGTH: 5
<212> TYPE: PRT
<213> ORGANISM: Artificial Sequence
<220> FEATURE:
<223> OTHER INFORMATION: linker

<400> SEQUENCE: 13

Gly Gly Gly Gly Ser
1               5


<210> SEQ ID NO 14
<211> LENGTH: 3
<212> TYPE: PRT
<213> ORGANISM: Artificial Sequence
<220> FEATURE:
<223> OTHER INFORMATION: linker

<400> SEQUENCE: 14

Gly Ser Gly
1


<210> SEQ ID NO 15
<211> LENGTH: 5
<212> TYPE: PRT
<213> ORGANISM: Artificial Sequence
```

<220> FEATURE:
<223> OTHER INFORMATION: linker

<400> SEQUENCE: 15

Gly Gly Ser Gly Gly
1 5

<210> SEQ ID NO 16
<211> LENGTH: 7
<212> TYPE: PRT
<213> ORGANISM: Artificial Sequence
<220> FEATURE:
<223> OTHER INFORMATION: linker

<400> SEQUENCE: 16

Gly Ser Gly Ser Gly Ser Gly
1 5

<210> SEQ ID NO 17
<211> LENGTH: 10
<212> TYPE: PRT
<213> ORGANISM: Artificial Sequence
<220> FEATURE:
<223> OTHER INFORMATION: linker

<400> SEQUENCE: 17

Gly Ser Ala Gly Ser Ala Ala Gly Ser Gly
1 5 10

<210> SEQ ID NO 18
<211> LENGTH: 8
<212> TYPE: PRT
<213> ORGANISM: Artificial Sequence
<220> FEATURE:
<223> OTHER INFORMATION: linker

<400> SEQUENCE: 18

Val Pro Leu Ser Arg Thr Val Arg
1 5

<210> SEQ ID NO 19
<211> LENGTH: 585
<212> TYPE: PRT
<213> ORGANISM: Artificial Sequence
<220> FEATURE:
<223> OTHER INFORMATION: Serum albumin

<400> SEQUENCE: 19

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ala Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525
```

-continued

```
Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585


<210> SEQ ID NO 20
<211> LENGTH: 4
<212> TYPE: PRT
<213> ORGANISM: Artificial Sequence
<220> FEATURE:
<223> OTHER INFORMATION: linker

<400> SEQUENCE: 20

Gly Gly Gly Ser
1
```